(12) United States Patent
Bovero et al.

(10) Patent No.: US 10,132,758 B2
(45) Date of Patent: Nov. 20, 2018

(54) SYSTEMS AND METHODS FOR CONSTRUCTING AND TESTING COMPOSITE PHOTONIC STRUCTURES

(71) Applicant: Saudi Arabian Oil Company, Dhahran (SA)

(72) Inventors: Enrico Bovero, Dhahran (SA); Vincent Brian Cunningham, Abqaiq (SA); Ilham Mokhtari, Dhahran (SA); Aziz Fihri, Dhahran (SA); Remi Mahfouz, Thuwal (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 0 days.

(21) Appl. No.: 15/644,919

(22) Filed: Jul. 10, 2017

(65) Prior Publication Data

US 2017/0307540 A1 Oct. 26, 2017

Related U.S. Application Data

(62) Division of application No. 15/082,327, filed on Mar. 28, 2016, now Pat. No. 9,816,941.

(51) Int. Cl.
*G01N 21/88* (2006.01)
*G02B 27/42* (2006.01)
(Continued)

(52) U.S. Cl.
CPC ....... *G01N 21/8851* (2013.01); *G01B 11/165* (2013.01); *G01L 1/00* (2013.01);
(Continued)

(58) Field of Classification Search
CPC ...... G01N 21/8851; G01L 1/00; G01B 11/165
(Continued)

(56) References Cited

U.S. PATENT DOCUMENTS 4,939,368 A 7/1990 Brown
6,355,420 B1* 3/2002 Chan .................... C12Q 1/6809
435/6.12
(Continued)

FOREIGN PATENT DOCUMENTS

DE 102010019247 A1 11/2011

OTHER PUBLICATIONS

Forsyth et al. "Dual Temperature and Strain Measurement with the Combined Fluorescence Lifetime and Bragg Wavelength Shift Approach in Doped Optical Fiber." Applied Optics, vol. 41, No. 31, Nov. 1, 2002, 8 pages.
(Continued)

*Primary Examiner* — Roy M Punnoose
(74) *Attorney, Agent, or Firm* — Leason Ellis LLP

(57) ABSTRACT

Systems and methods are disclosed relating to composite photonic materials used to design structures and detecting material deformation for the purpose of monitoring structural health of physical structures. According to one aspect, a composite structure is provided that includes a base material, an optical diffraction grating and one or more fluorophore materials constructed such that localized perturbations create a measurable change in the structure's diffraction pattern. An inspection device is also provided that is configured to detect perturbations in the composite structure. The inspection device is configured to emit an inspecting radiation into the structure and capture the refracted radiation and measure the change in the diffraction pattern and quantify the perturbation based on the wavelength and the angular information for the diffracted radiation.

15 Claims, 27 Drawing Sheets

(51) Int. Cl.
  *G02B 5/18*   (2006.01)
  *G01N 21/47*  (2006.01)
  *G01L 1/00*   (2006.01)
  *G01B 11/16*  (2006.01)
(52) U.S. Cl.
  CPC ....... *G01N 21/4788* (2013.01); *G02B 5/1861* (2013.01); *G02B 27/4244* (2013.01); *G01N 2201/0635* (2013.01)
(58) Field of Classification Search
  USPC ..................................................... 356/239.1
  See application file for complete search history.

(56) References Cited

U.S. PATENT DOCUMENTS

| | | | | |
|---|---|---|---|---|
| 9,816,941 B2* | 11/2017 | Bovero | .............. | G01N 21/8851 |
| 2012/0007000 A1* | 1/2012 | Lu | ...................... | G01N 21/6428 |
| | | | | 250/458.1 |

OTHER PUBLICATIONS

International Search Report and Written Opinion for International Patent Application No. PCT/US2017/024278 dated Jun. 29, 2017. 15 pages.

\* cited by examiner

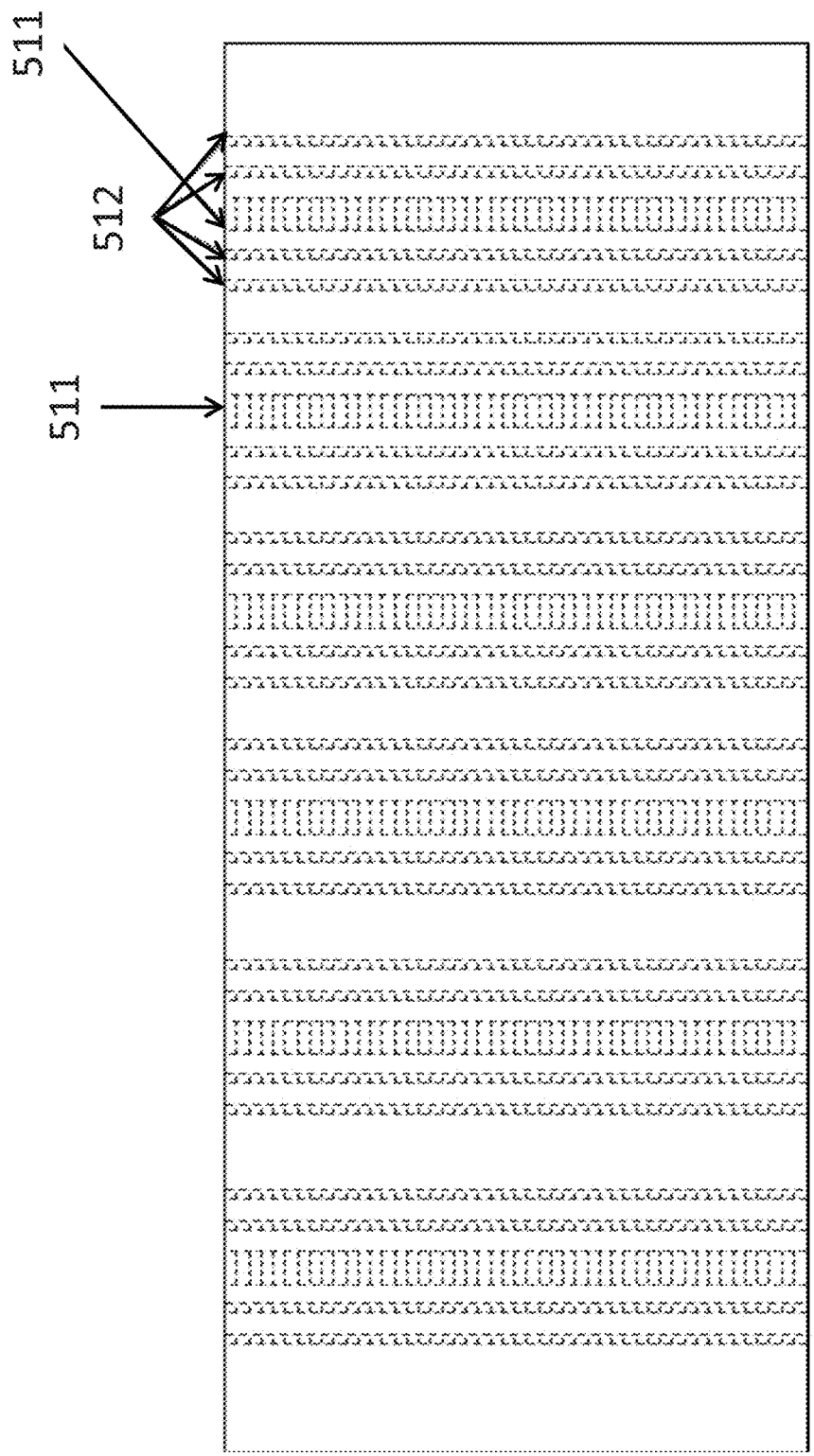

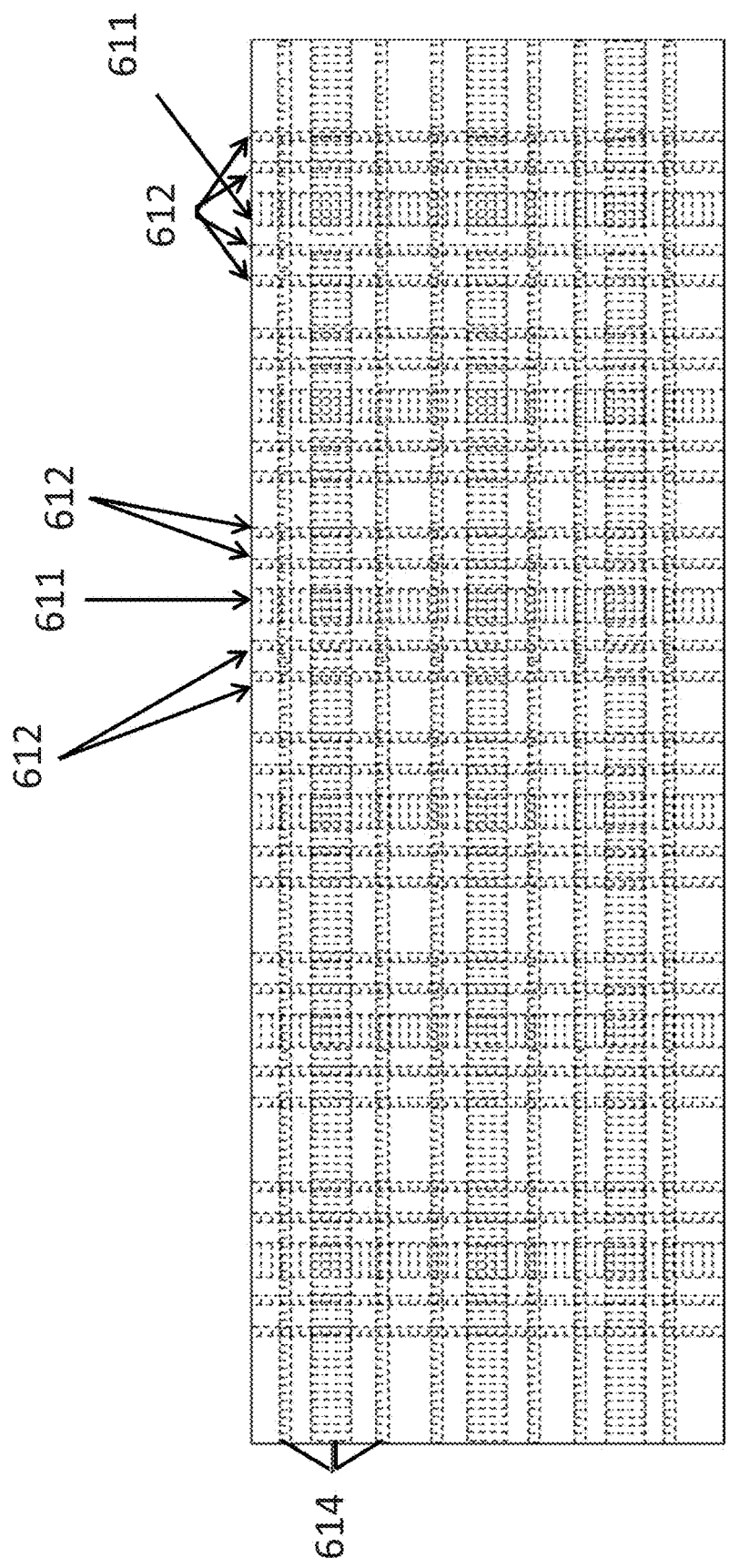

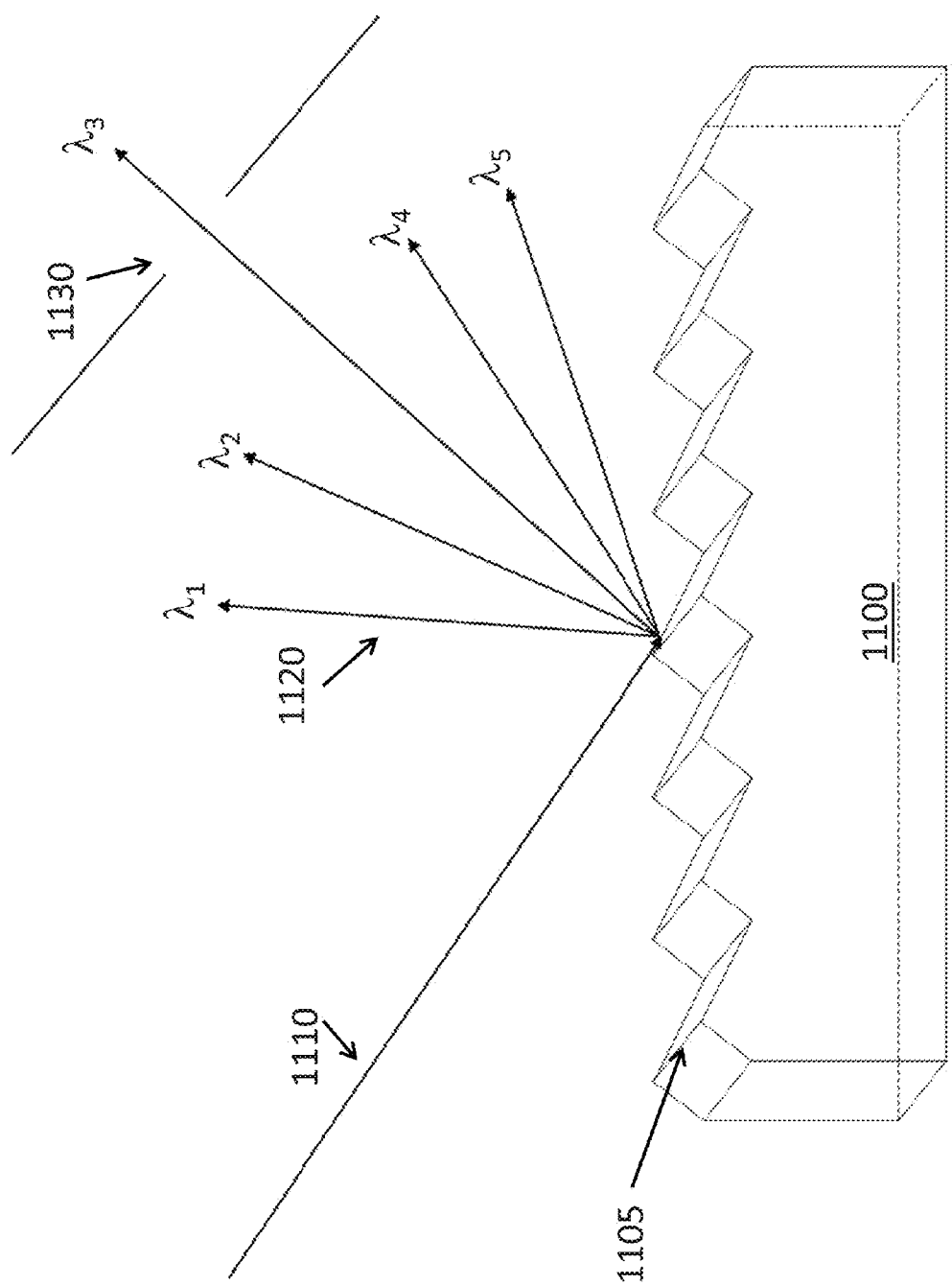

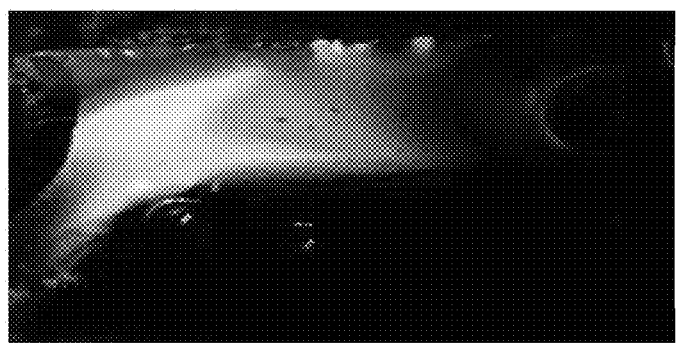
FIG. 16B With Stress
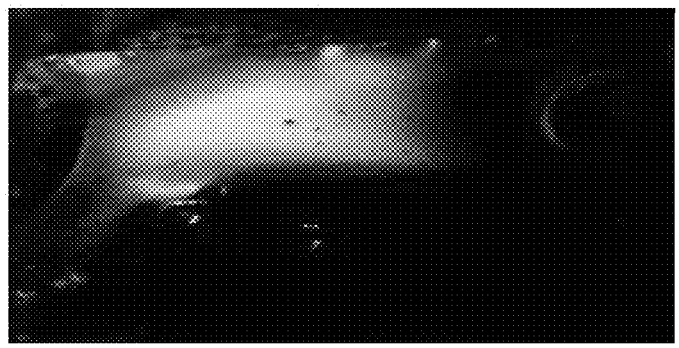
FIG. 16A Without Stress

SYSTEMS AND METHODS FOR CONSTRUCTING AND TESTING COMPOSITE PHOTONIC STRUCTURES

CROSS REFERENCE TO RELATED APPLICATIONS

The present application is a divisional application of U.S. patent application Ser. No. 15/082,327 filed on Mar. 28, 2016, entitled SYSTEMS AND METHODS FOR CONSTRUCTING AND TESTING COMPOSITE PHOTONIC STRUCTURES, the contents of which is hereby incorporated by reference as if set forth in its entirety herein.

FIELD OF THE INVENTION

The present invention relates to composite photonic structures and non-destructive inspection systems and methods, in particular to systems and methodologies for constructing composite photonic structures and inspection systems and methods for detecting perturbations in the structures for the purpose of structural health monitoring.

BACKGROUND

The availability of non-destructive inspection techniques for structural materials, for instance, nonmetallic pipes used in pipelines, is limited. For the most part, the techniques available so far are either destructive to the material or are experimental and unreliable. Even considering current experimental techniques for non-destructive inspection, no current techniques are able to reliably predict the formation of defects, and are generally used to detect only existing defects.

More specifically, existing building materials and the corresponding systems and techniques for inspection of the materials are inadequate for detecting the presence of stresses on or in the material such as tensile stress or compressive stress with sufficient accuracy and precision such that defects can be predicted before they occur.

Currently available technologies for sensing material defects are generally based on mono-dimensional fiber Bragg gratings. These fibers provide mono-dimensional information: i.e., they can detect only stress that occurs along the length of the fiber, and only substantial stresses that correspond to already damaged materials with significant cracks and ruptures in the structural material.

There is a need for systems and methods for detecting perturbations in structural materials that utilize a photonic material, such as an optical grating or a photonic crystal, as a sensitive element for diffraction generation. In addition, there is a need for systems and methods for detecting perturbations in structural materials that quantify deformations in photonic materials through a wavelength change, or a diffraction angle change quantified from an intensity variation. Moreover, there is a need for systems and methods for detecting perturbations with a sensitivity that is tunable through the choice of the inspecting wavelength and the corresponding periodicity of the photonic structural material. In addition, there is a need for systems and methods for detecting perturbations that have a multi-dimensional level of sensitivity.

It is with respect to these and other considerations that the disclosure made herein is presented.

SUMMARY

According to an aspect of the present invention, there is provided a composite photonic structure which comprises one or more layers of a non-metallic structural material, a diffractive refractive grating in registry with at least one layer of structural material, and one or more fluorophore materials disposed within the composite structure. The grating includes a plurality of features that are arranged to have periodicity in at least one dimension.

According to a further aspect, the grating can comprise a discrete layer of one or more grating materials disposed over an entire surface of at least one layer of the structural material, a surface of at least one layer of the structural material, or a combination of these constructions. The grating in this or other embodiments can extend over a top surface, a bottom surface, or both surfaces of at least one of the layers of structural material. In still further aspects, the grating layer can separate two layers of the structural material, and the plural features of the grating can be arranged to have periodicity in at least two dimensions.

In further aspects, alone or in combination with the foregoing, the fluorophore can comprise a fluorophore that is excited by radiation having a first wavelength and which emits radiation having a second wavelength upon excitation, wherein the one or more layers of structural material and the grating are transparent to radiation having the first and second wavelengths. In certain embodiments, the fluorophore can be incorporated into the composite structure as a separate layer of material that includes at least the fluorophore material, as a dopant or nano-material that is embedded in a region within at least one of the one or more layers of structural material, or a combination of the foregoing.

In still further aspects, a device for non-destructive inspection of a photonic structure having a periodic refraction grating is provided which comprises a lamp configured to emit a cone of radiation toward and onto a portion of a sample, the radiation having constant intensity over a range of wavelengths. A camera sensor is configured to capture an image of diffracted radiation, wherein the diffracted radiation is the radiation emitted by the lamp as diffracted by the portion of the sample, and wherein the image provides one or more wavelengths of the radiation captured at each respective point on the captured image. A computer readable storage medium including one or more software modules including an analysis module is included, wherein each module includes executable code. A processor is communicatively coupled to the lamp, the camera sensor and the storage medium, wherein the processor is configured by executing the code in the one or more software modules to analyze the image of the captured radiation in order to determine a displacement of any perturbations within the portion of the sample by, for each point on the captured image: transforming the wavelength at the point to a first periodicity value for a corresponding point within the portion of the sample as a function of a position of the lamp and the camera sensor relative to the sample and a diffraction angle for the corresponding point within the portion of the sample, and computing an amount of deformation for the corresponding point based on the first periodicity value and a reference periodicity. A visual display is in signal communication with the processor, wherein the processor is configured to output an image of the sample representing the amount of deformation computed for each corresponding point within the portion of the sample using the display.

An inspection device according to still further aspects can further comprise a laser emitter configured to emit a beam of radiation having a specific wavelength onto a particular location on the sample and a detector configured to capture at least one diffracted beam and measure an intensity of the at least one captured beam and a corresponding position on the detector, wherein the at least one diffracted beam is a result of the sample diffracting the emitted beam. In such an inspection device, the processor is further configured by executing the one or more software modules to receive the measured intensity and the corresponding position for the at least one captured beam and determine a displacement of any perturbations at the particular location on the sample by: calculating a diffraction angle for the particular location on the sample as a function of the corresponding position of the at least one captured beam, and calculating a second periodicity value for the particular location on the sample according to the calculated diffraction angle and a prescribed grating characteristic of the sample, and computing an amount of deformation for the particular location based on a difference between the second periodicity value and a reference periodicity for the particular location.

These and other aspects, features, and advantages can be appreciated from the accompanying description of certain embodiments of the invention and the accompanying drawing figures and claims.

BRIEF DESCRIPTION OF THE DRAWINGS

FIG. 5B depicts a top view of an exemplary diffraction pattern caused by the embodiment of FIG. 5A;

FIG. 6B depicts a top view of an exemplary diffraction pattern caused by the embodiment of FIG. 6A;

FIG. 11A is a high-level diagram illustrating an exemplary configuration of a monochromator utilizing a stretchable grating as a diffraction element;

FIG. 16A is a screenshot of an exemplary wavelength map as captured by an exemplary inspection device according to an embodiment of the invention;

FIG. 16B is a screenshot of an exemplary wavelength map as captured by an exemplary inspection device according to an embodiment of the invention;

DETAILED DESCRIPTION OF CERTAIN EMBODIMENTS OF THE INVENTION

Figure 1:
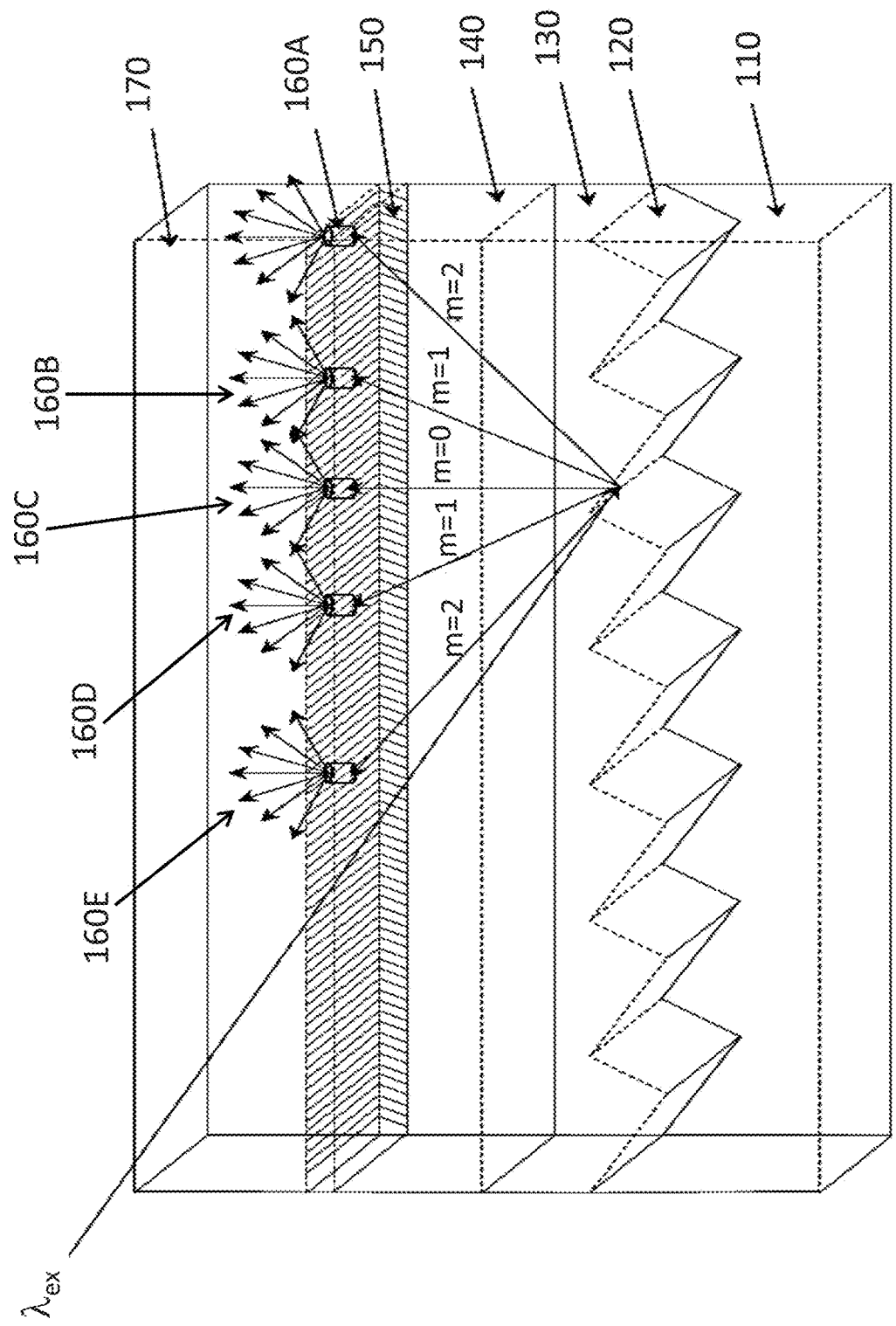
FIG. 1 is a high-level diagram illustrating an exemplary composite structure with a fluorescent layer and a two dimensional grating with one dimensional periodicity according to an embodiment of the invention.

By way of overview and introduction, systems and methodologies for detecting material deformation primarily for the purpose of structural health monitoring are disclosed herein. According to a first aspect, a composite material/structure that can be used to construct engineered structures is disclosed. The composite includes a base material (e.g., a structural material such as a non-metallic plate or pipe), an optical diffraction grating and one or more fluorophore materials. In some implementations, the composite structure does not include a fluorescent material. In some implementations, the grating can be a surface of the base material or a separate layer of material (e.g., a thin layer of aluminum). The materials of the composite structure are arranged such that deformation of one or more of the materials of the composite structure, e.g., perturbations caused by, for example and without limitation, tensile stress, compressive stress, bending, temperature variations, and chemical composition changes and other material defects, locally changes the periodicity of the grating, or the refractive index of one or both materials, for instance, by changing the size of the features and/or the relative distance between the features of the grating. This creates a measurable change in the diffraction pattern caused by composite structure that is proportional to the size of the perturbation and, using an inspection device, can be quantified as a wavelength shift for a specific angle of diffraction according to the expected diffraction characteristics of the grating as defined by a gratings equation.

The fluorophore or fluorophores can be inserted into the base material as dopants, nano-materials, or provided as a discrete material layer that is separate from the base material. In addition or alternatively, one or more layers of fluorophore material can be embedded in the grating material or a surrounding layer of material.

According to another aspect, devices and methods for non-destructive inspection of the exemplary composite structures are also disclosed herein. The inspection device is configured to detect perturbations in the composite structure based on diffraction of an inspecting radiation and the radiation generated by fluorophores within the composite structure. More specifically, the inspection device is configured to emit an inspecting radiation onto or into the composite structure and capture the diffracted radiation as an input and measure the change in the diffraction pattern from an expected pattern. It can be appreciated that changes in one or more boundary behaviors of the radiation waves can occur and be captured and measured. Changes in behavior include diffraction, reflection and refraction of the radiation and one or more of the foregoing behaviors, and combinations thereof, can be measured, for instance, the inspecting radiation can be reflected and diffracted, or refracted, reflected and diffracted, or refracted and diffracted etc. Accordingly, it can be appreciated that the common phenomenon is the diffraction of the radiation.

The inspection device provides as an output, a quantification of the perturbation affecting the composite structure. In particular, the inspection device transforms the wavelength and/or the angle information into a measure of displacement. The inspection device consists of one or two components together utilizing two similar principles to achieve such a transformation. One component transforms the wavelength information into a displacement, while the other component transforms the angular information into a displacement. Each component can work independently from the other. The periodic structure considered could be for example a diffraction grating such as the one depicted in FIG. 1 and described herein.

The Composite Structure

As noted above, in accordance with one or more of the disclosed embodiments, the composite structure includes a base material (e.g., a structural material such as a metallic or, preferably, a non-metallic plate or pipe), an optical diffraction grating, or photonic crystal, and can also include a one or more fluorophore materials (e.g., . . . ). In some implementations, the grating can be a surface of the base material or a separate layer of material (e.g., a thin layer of aluminum, or any other reflective metal or material, etc.).

The grating does not have to be necessarily a material on its own, but can be defined by any interface with periodic features between materials with different refractive indices, one of which can also be air, or any other gas, or liquid. More in general the diffractive role played by the diffraction grating represented in FIGS. 1 to 7 can be performed by a photonic crystal. Such a photonic crystal can be defined as a periodic modulation of refractive index within a certain region of space that is able to generate a photonic band structure similar to the way in which a crystalline solid or semiconductor generates an electronic energy level structure, or electronic band structure (with conduction and valence bands). As an extension, any crystalline material can be also considered as a photonic crystal with a periodicity size in the order of Å that is able to generate a photonic band structure in the x-ray region of the spectrum, which is measurable by X-ray diffraction. In most cases the position of the photonic band gap, or the entire photonic band structure can be calculated according to literature using a combination of the Bragg's law for diffraction and Snell's law for refraction. In the majority of applications for human scale and interests, the size of the periodicity of the structure to detect defects can be tuned around the submicron to micron scale, which will generate response in the UV-visible to NIR range of the electromagnetic spectrum. However, applications beyond this range both at smaller and higher scales are also possible. The dimensionality of the system can range from 1D to nD. The practical periodicities are 1, 2, and 3 Dimensional. In 1 Dimension the photonic crystal can be represented as a Fiber Bragg Grating, a Photonic Crystal Fiber Bragg Grating, or anything whose periodicity varies along one direction. In 2 Dimension the photonic crystal can be a diffraction grating, or a monolayer of particles distributed periodically on a surface, or a periodic distribution of holes arranged in 2 Dimensions, as depicted in FIGS. 1 to 7, or also in this case a Photonic Crystal Fiber Bragg Grating. In 3 Dimensions the photonic crystal can be an Opal, or any periodic distribution of features that generate a modulation of the refractive index.

The one or more fluorophores to be inserted inside the photonic structure can be any active material with an emission wavelength able to interact with the photonic band structure generated by the periodic photonic structure and ultimately determined by the size of the periodicity, which in turn is determined by the degree of sensitivity required. The emission profile of the fluorophore can be very narrow or broad depending on the interaction mechanism with the photonic structure. For example, if the displacement is measured as intensity related to a change in the diffraction angle, a narrow emission profile of the fluorophore will result in a more sudden intensity change as a consequence of a displacement in the material. However, above a certain value of displacement, the intensity will be lost (because it will be deviated away from the photodetector, and thus the system won't be sensitive to even larger displacements. If the emission profile of the fluorophore is broad, the intensity change won't be as sudden, but it will be measurable for a larger range of displacement. On an even more sensitive scenario, a fluorophore could present multiple emission peaks, so that the change in intensity is sharp for small displacements, while it remain sensitive even for larger displacements, as another emission peak will collide with the detector. The same result can be obtained by inserting different fluorophores into the same structure. For these reasons, the fluorophores can be organic molecules with broad and intense emission bands, or transition metal ions, or Lanthanide ions with sharp emission peaks, or Quantum Dots, or semiconductor nanocrystals with emission bands determined by quantum confinement and thus tunable both in energy and to a certain extent in broadness.

The size of the periodic features of the grating are comparable in size to the size of the perturbation to be detected, in one embodiment. Furthermore, it such an embodiment the material constituting the grating can have a flexibility which is sufficient to respond to a perturbation within itself or within its surroundings.

Such a composite structure can be configured to work both in reflection and in transmission mode. The materials that define the composite, in one implementation, is of the type that allows the inspecting radiation to pass therethrough. In this or other implementations, the grating can be shaped out of one material attached or placed in proximity to another material, or it can be fabricated as the interface between two materials with different refractive indices.

In one exemplary configuration, the fluorophore has a narrow emission band so as to improve detection of the fluorophore when excited. In addition, the fluorophore can be placed on the opposite side of the base material with respect to the inspection device. Accordingly, the base material, grating and fluorophore are selected to allow transmission of the inspecting radiation and radiation emitted by the fluorophore. This exemplary composite structure configuration can enhance sensitivity and simplify the detection of perturbations in the material. The reason is that the aforementioned wavelength shift for a quasi-monochromatic radiation will result in the presence or absence of radiation as a result of a small perturbation. Such a change is easier to detect because: it provides a higher sensitivity contrast; can be detected as a simple change in intensity rather than wavelength shift, thus simplifying the detection system and reducing its cost; it eliminates the need of a broad band excitation source; and the excitation source and detection system can be placed on the same side with respect to the grating, and can be incorporated into a single device, without losing angular resolution or sensitivity contrast.

These and other exemplary configurations in which one or more layers of base material, fluorophore and the grating surface are layered are further described more specifically herein. These configurations include various two and three dimensional arrangements of the one or more fluorophores within the composite, for instance, as parallel rods, perpendicular meshes and three dimensional lattices. According to a further aspect, the composite can include one or more photonic crystals and quantum dots to define the grating layer and, in some implementations, the fluorescent layer as well.

In accordance with one or more of the disclosed embodiments, an exemplary configuration of the composite can include a regular two dimensional grating with periodicity along one direction and the one or more fluorophores can be embedded in a material layer parallel to the surface of the grating. A composite structure 100 having such a configuration is represented in FIG. 1.

From the embodiment of FIG. 1 it is possible to appreciate few of the advantages of the invention. The grating 120 in this case is formed between material 110 and material 130. Material 110 and 130 present different refractive indices. Material 110 can also be air, while material 130 could in principle be air but more commonly a solid material. The grating surface 120 can be the simple interface between the two materials or made by a thin layer of another material such as for example Aluminum. The material 140 is not necessary for the purpose of the device, but it is defined in case the fabrication procedure includes the fabrication of the grating as a standalone piece made of material 130. Material 150 contains one or more fluorophores. It can be the same material as material 140, which in turn, as aforementioned, can be the same material as material 130. The one or more fluorophores can be inserted in material 150 as a dopant, a nano-material, or material 150 can be fluorescent itself. Material 170 can be a protection layer for the fluorescent layer, or it can be absent. The optical characteristics of materials 110, 130, 140, 150, and 170, in certain implementations, have at least partial transparency at the wavelength of excitation of the one or more fluorophores and also at its emission wavelength.

In operation, as the radiation of excitation, represented as $\lambda_{ex}$ (e.g., radiation emitted by an inspection device), reaches the grating surface 120, a diffraction pattern is generated both in reflection and transmission mode. As would be understood by those in the art, a grating responds to a white light source by decomposing it into different wavelengths, while a grating responds to a laser beam by diffracting it into separate beams emerging from the grating at different angles depending on the diffraction order. As shown in FIG. 1, the inspection radiation is a beam $\lambda$, emitted by a laser source of an inspection device (not shown). In the exemplary embodiment shown in FIG. 1, only the reflection mode is considered and the "m" values in the figure represent the orders of diffraction for respective diffracted beams. As shown, the diffracted beams (e.g., m=0, 1, 2) reach the fluorescent layer at different positions determined by the structure of the grating. In these positions the fluorescent layer will emit radiation producing a 1 or 2 dimensional image of such pattern that can be imaged/captured by a specially configured inspection device, as further described below. Any perturbation in the material such as defects, compressive and tensile stresses, bending, and twisting will affect the diffraction pattern and thus the image formed by the fluorescent layer. The spots 160A-160E shown in FIG. 1 are the regions of the fluorescent layer through which the diffracted radiation is passing or absorbed and that are emitting radiation as a result of being exited by the diffracted radiation.

As a consequence of a perturbation in the so constructed composite structure and, more specifically perturbation affecting the periodicity of the grating surface 20, the parameters that can change in the diffraction pattern are: the distance between each spot, the size and shape of each spot, and with it, the intensity distribution. As a result, analysis of the reflection to detect such perturbations can include monitoring the intensity or radiation in a particular point, within one or more of: the emitting spot, at a specific distance or relative to the excitation beam. In this way the detector can be mounted and fixed on the same device containing the excitation source. The changes in intensity measured at that specific point, not only indicate the presence of a perturbation but also the extent of the perturbation, and the type of perturbation. For example, a tensile stress can push the spots 160A-160E apart from each other therefore it will result in a decrease in intensity of radiation on the left side of the spot 6A (on the far right in FIG. 1), or an increase on that spot's right side. A similar response can be caused by a bending force that generates a convex, or negative, curvature in the grating. The opposite response can occur if the stress is compressive or if the bending is causing a positive curvature on the grating. In the case of twisting the spot will move sideways and the intensity will change according to the same principle.

Figure 2:
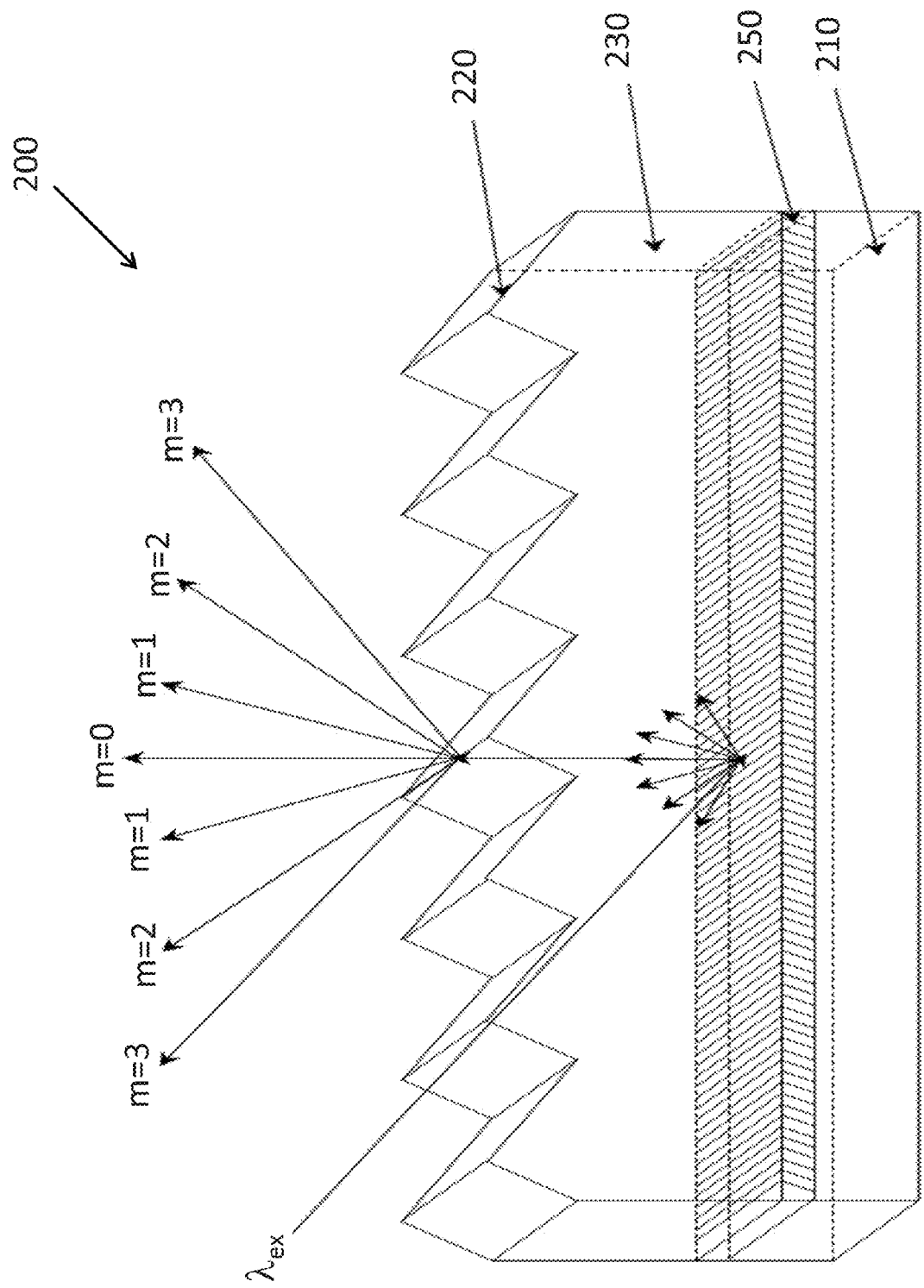
FIG. 2 is a high-level diagram illustrating an exemplary composite structure with a fluorescent layer and a two dimensional grating with one dimensional periodicity according to an embodiment of the invention.

FIG. 2 depicts another exemplary configuration of the composite in accordance with one or more embodiments of the invention. In particular, as shown in FIG. 2, the fluorescent layer 250 is placed below the grating surface 220. Material 210 can be the base support for the entire composite structure and material 250 is the material layer including fluorescent material. In some implementations it can be a material that contains one or more fluorophores or it can be a fluorescent itself. In addition or alternatively, material 210 is not necessarily included, as material 250 can perform the function of base material and the one or more fluorophores can be contained within material 250. Material layer 230 provides a separation between the fluorescent layer and the grating. Also this material is not strictly necessary, however, in practical applications material layer 230 can provide a useful separation and further support layer. Finally, the grating surface 220 is on top and, in some implementations, can be made of a separate material from material 230 or it can be shaped out of material 230.

Figure 3:
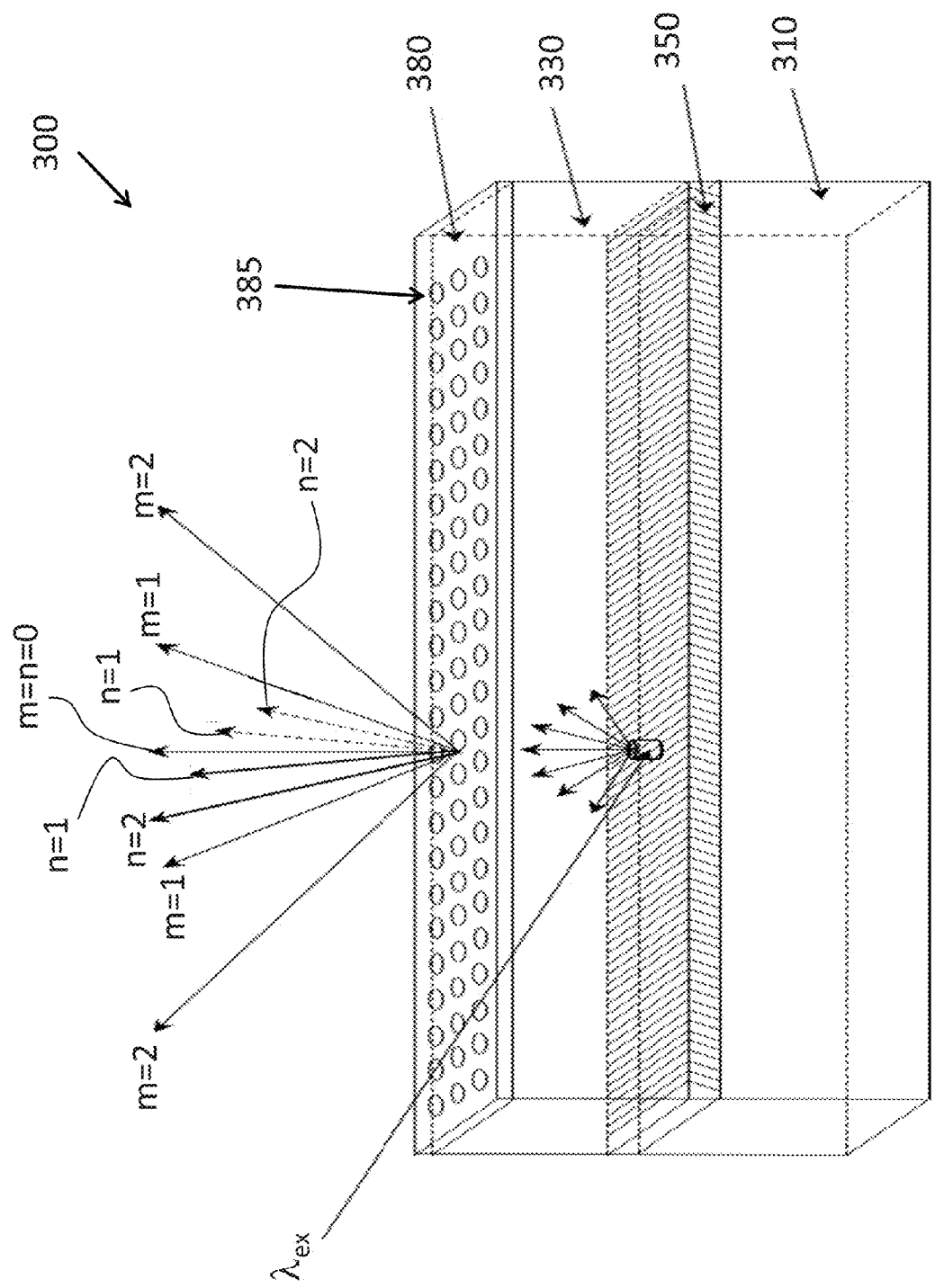
FIG. 3 is a high-level diagram illustrating an exemplary composite structure with a fluorescent layer and a two dimensional grating with two dimensional periodicity according to an embodiment of the invention.

FIG. 3 depicts another exemplary configuration of a composite structure 300 in accordance with one or more embodiments of the invention. As shown in FIG. 3, the fluorescent layer 350 is placed below the grating 380. Material 310 can be the base support for the entire composite structure and material layer 330 can be the structural material. As shown, material layer 350 is the layer including the fluorescent material. Moreover, as shown in FIG. 3, the grating 380 utilized is two dimensional, such as, for example, a periodic distribution of holes within a slab of another material. As a result, this will generate a two dimensional diffraction pattern, which will allow for a more direct way to detect anisotropy of perturbation in the grating or in the material with which the grating is in contact. The holes depicted in the figure (e.g., hole 385), can be actual holes or regions made of a material having a different refractive index from the remaining material defining the grating. In one or more implementations, the optical characteristics of this top layer having holes or such regions include: a material that is transparent for the excitation radiation, unless the radiation is directed to pass through a gap in it; a material having a different refractive index with respect to the rest of the layer; and a material that is at least partially transparent for the wavelength of the emitted radiation.

In FIGS. 1, 2 and 3 it is indicated the different orders of diffraction m=1, . . . n, and "n" is truncated to two for easiness of depiction in the figures, however, the useful diffraction order can reach higher order depending on the structure of the grating, the distance between the fluorescent layer and the grating, the distance between the grating and the observer (e.g., inspection device), and in general the architecture of the device and the detection system. While the grating depicted in FIG. 1 presents a mono-dimensional periodicity and the grating in FIG. 3 presets a two-dimensional periodicity, a grating having any type of periodicity can be used for the two exemplary composite architectures, depending on the diffraction characteristics desired. The advantage of a grating with two-dimensional periodicity is that it will generate a diffraction pattern with information about the two dimensional anisotropy of the stress. For example, in the case of a tensile stress along a particular direction, the distance increase between the diffraction spots will be only along that particular direction.

Figure 4:
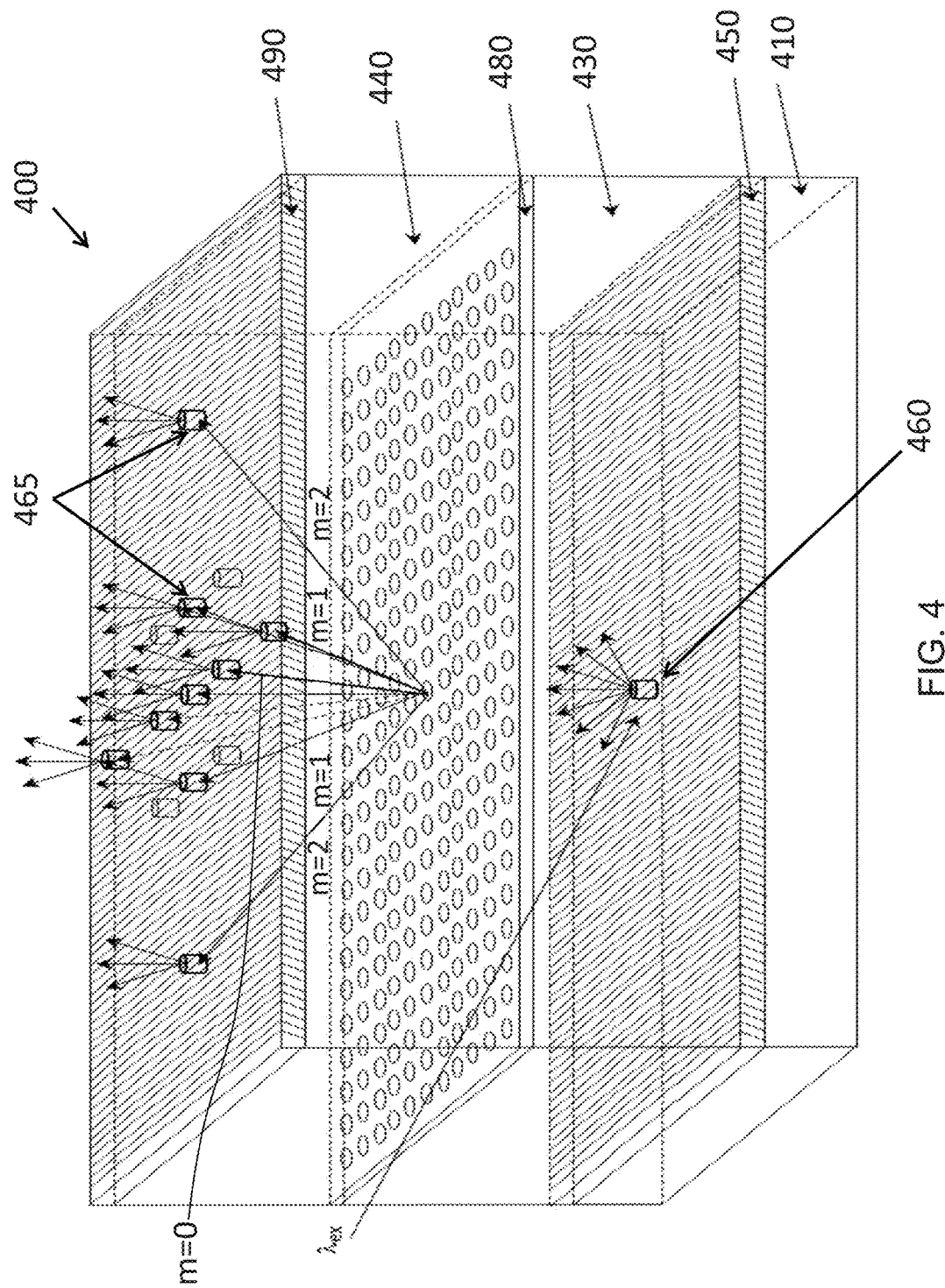
FIG. 4 is a high-level diagram illustrating an exemplary composite structure with two fluorescent layers and a two dimensional grating with two dimensional periodicity according to an embodiment of the invention.

In another exemplary embodiment of the invention, as shown in FIG. 4, a composite structure 400 can include two fluorescent layers. The construction of the composite 400 shown in FIG. 4 is similar to the exemplary configuration shown in FIG. 2 that has a fluorescent layer below the grating surface but also includes a second fluorescent layer 490 above the grating. More specifically, bottom layer 410 can serve as a support for the fluorescent layer 450 and, in some variations, is not necessary if the material layer 450 that includes one or more fluorophores is configured to be a structural material layer including one or more fluorophores therein. Layer 430 is a separation layer between the fluorescent layer 450 and the grating layer 480. Layer 480 is the grating, which as shown, can be a separate material layer. However, in some implementations, separation layer 430 and 480 can be combined, except that the holes shown in grating layer 480 can comprise a material with a different refractive index. Layer 440 is a separation layer between the grating and the second fluorescent layer and can be either a structural material layer or, in some implementations, air. Finally layer 490 is an additional top fluorescent material layer.

The purpose of this added fluorescent layer 490 is to simplify the visualization of the diffraction pattern and thus the detection of perturbations in the composite structure system. In operation, a radiation $\lambda_{ex}$ can be shone through the structure 400 onto a spot 460 on the fluorescent layer 450. The excited fluorescent spot 460 emits light in all direction and partially passes through layer 430 and crosses the grating 480. At this point, due to the diffraction grating, the radiation is diffracted and proceeds through layer 440 toward layer 490 as individual beams, shown as m=0 through m=2. Due to the additional fluorescent layer 490, these beams are visualized as fluorescent spots 465 shown by the top fluorescent layer 490. The purpose of this top fluorescent layer 495 is to facilitate the visualization of these beams.

The excitation radiation is selected such that its wavelength is not completely absorbed by the layers of material comprising the composite 400 through which the radiation passes, except fluorophore layer 450. Minimal or no radiation absorption in the non-fluorescent layer(s) is preferable in order to ensure that the fluorescent layer 450 receives the excitation radiation. The fluorescent material 450 is also selected such that its wavelength of emission from layer 450 (the "first emission radiation") also passes undisturbed through layer 430, which is preferably at least partially transparent for this wavelength of radiation. The layer 480 could be made of two materials with different refractive indices, or the cylindrical holes can be simply empty. Both materials are preferably transparent to the excitation radiation, while, with respect to the emission radiation, they can be either transparent or at least the material constituting the cylindrical holes in the figure needs to be at least partially transparent.

In the case that the grating 480 is not a two dimensional photonic crystal, as shown in FIG. 4, but instead is a grating surface like the grating 120 depicted in FIG. 1, the requirement is that both material 430 and 440 are be at least partially transparent for the first emission radiation. With such an architecture, layer 480 need not be a discrete layer and can be a grating surface separating (e.g., defining the interface between) layer 430 and 440. Layer 440, in any case should be transparent for the same radiation emitted by layer 450. Layer 480 can also be a three dimensional photonic structure, in this case similar considerations as for the grating displayed in FIG. 4 are valid regarding the transparency of the two constituent materials. The fluorescent layer 490 can be selected such that it absorbs the emission radiation from 450 and is excited by the emission radiation and, as such, emits a second emission radiation with a different wavelength than the first emission radiation. Alternatively, the top layer 490, instead of being a fluorescent layer, can be simply a screen on which the image is visualized.

In some exemplary arrangements, a composite can be constructed such that the grating is above the one or more fluorophores and the one or more fluorophores are arranged within the material in such a way that they do not extend through the entire area of a surface of the material below the grating. An exemplary configuration of a composite structure 500 having such a configuration in accordance with one or more embodiments of the invention is shown in FIG. 5A.

Figure 5A:
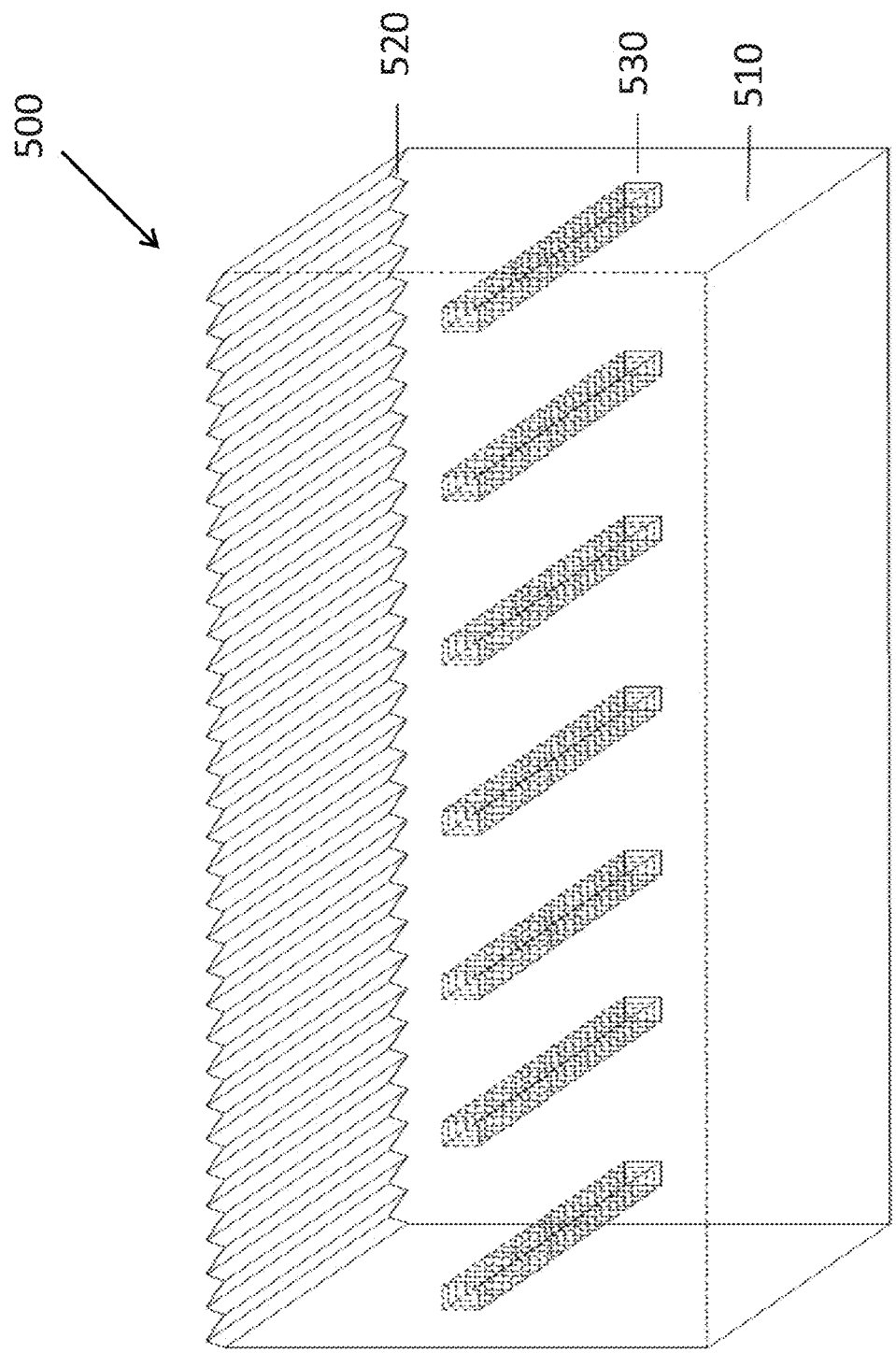
FIG. 5A is a high-level diagram illustrating an exemplary composite structure with structured parallel strips of fluorescent material and a two dimensional grating with one dimensional periodicity according to an embodiment of the invention.

As shown in FIG. 5A, the fluorescent portion of the material is an arrangement of parallel strips 530 embedded within the structural material 510 and below the grating surface 520, which defines the top surface of the material layer 510. The inspection illumination in this case does not have to be a laser, but it can be a lamp emitting light including an excitation wavelength that is chosen based on the one or more fluorophores utilized (e.g., based on its particular excitation wavelength). In this way the strips of fluorescent material inside the material 530 will appear to light up upon excitation. FIG. 5B depicts a top view of the diffraction pattern that is formed by the set of parallel fluorescent rods embedded periodically below the grating. As shown, the radiation from each of the excited fluorescent rods show as respective strips 511. In addition, the areas in between the fluorescent stripes (e.g., strips 512) will also present lines of emission as a result of the diffraction of the fluorescent lines from the grating. By monitoring these lines and the pattern formed, it is possible to detect any deformation, as a deformation of the material would cause a movement, a change of shape, or a shift of these lines from the expected pattern. For these reasons, from a detection point of view, it is possible to monitor only one spot and detect the change of emission intensity coming from that specific spot. Therefore, a deformation could be detected as an interruption of signal or as a start of signal.

Figure 6A:
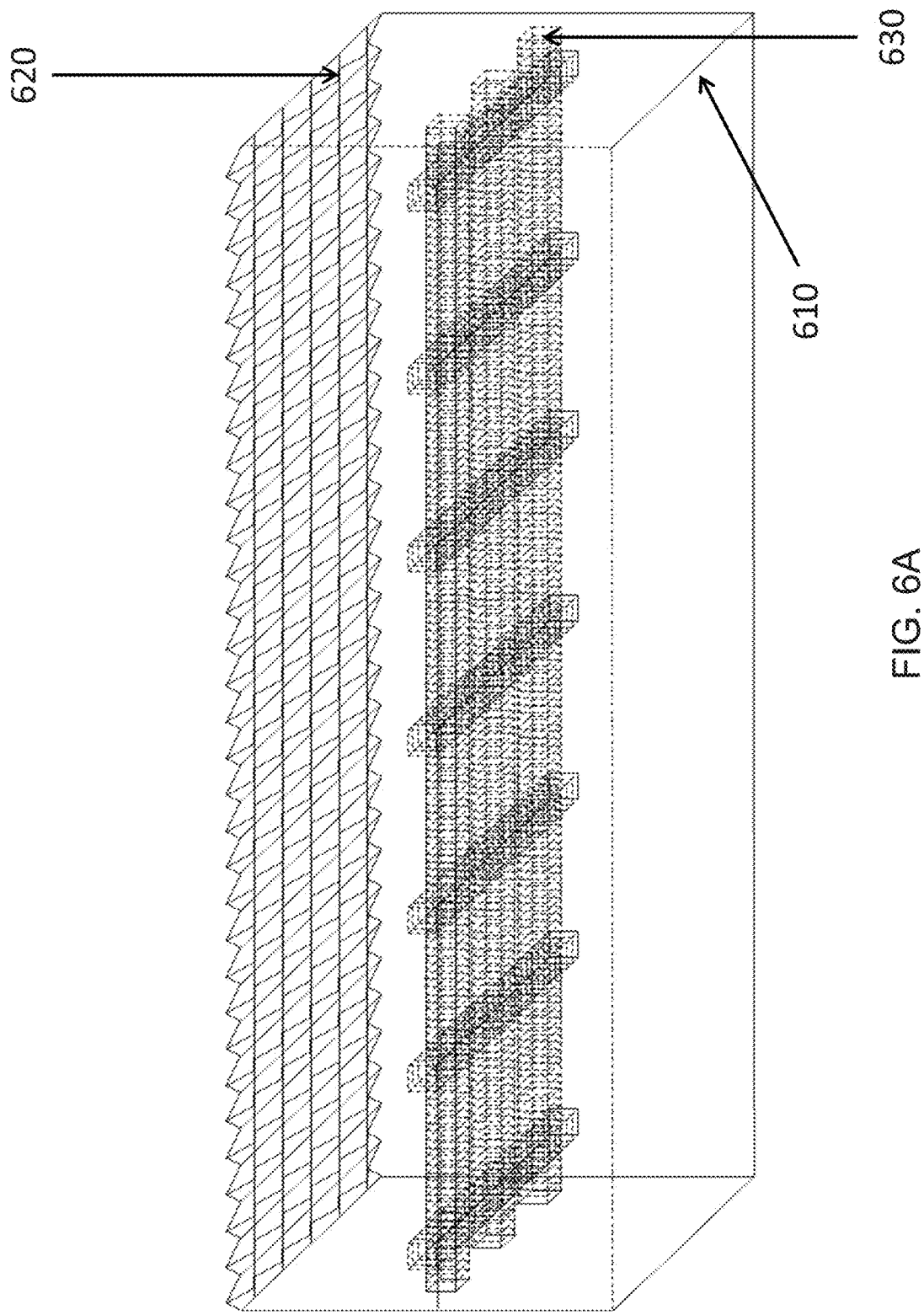
FIG. 6A is a high-level diagram illustrating an exemplary composite structure with two perpendicular sets of structured strips of fluorescent material and a two dimensional grating with two dimensional periodicity according to an embodiment of the invention.

Further to the foregoing example in which the fluorescent materials are arranged within the structural material according to a pattern having periodicity in one direction, different fluorescent patterns can be used to create the composite structure depending on the anisotropy of the information desired. FIG. 6A, depicts an exemplary configuration of a composite structure 600 formed of a structural material 610 having a top grating surface 620 and embedded fluorescent material 630 therein. As shown, the fluorescent material is arranged as two sets of parallel lines (that each have a width and a thickness) that are perpendicular to one another and the grating surface is a two dimensional grating with two dimensional periodicity. FIG. 6B depicts a top view of the composite structure and depicts the diffraction pattern that is formed by the two sets of parallel fluorescent lines that are oriented perpendicularly to one another. In particular, lines 611 correspond to the emitted radiation from the fluorescent lines oriented across the length of the structure 600 and the lines 612 formed in the area in between the fluorescent stripes are lines of emission as a result of the diffraction of the fluorescent lines from the grating 620. A similar pattern of radiation lines 614 are also emitted by the length-wise fluorescent strips. In use, parallel lines of fluorescent material can be useful to detect perturbations perpendicular to them, as a perturbation along the same direction would have little effect on them. Alternatively, a grating made of two sets of parallel lines perpendicular to each other can provide information regarding perturbations affecting the material in one or more of two directions of space.

Accordingly, a so constructed material, can be monitored and its particular construction used to detect the amount of perturbation, stress, or deformation to which the material is exposed. In particular, the exemplary construction makes it possible to quantify the extent of deformation. For example, if the material only includes a grating, any deformation will result in a wavelength change. On the other hand, in the presence of one or more fluorophores in addition to the grating, the deformation will change the spacing between the diffraction lines or the angle between the beams diffracted from the grating.

Figure 7:
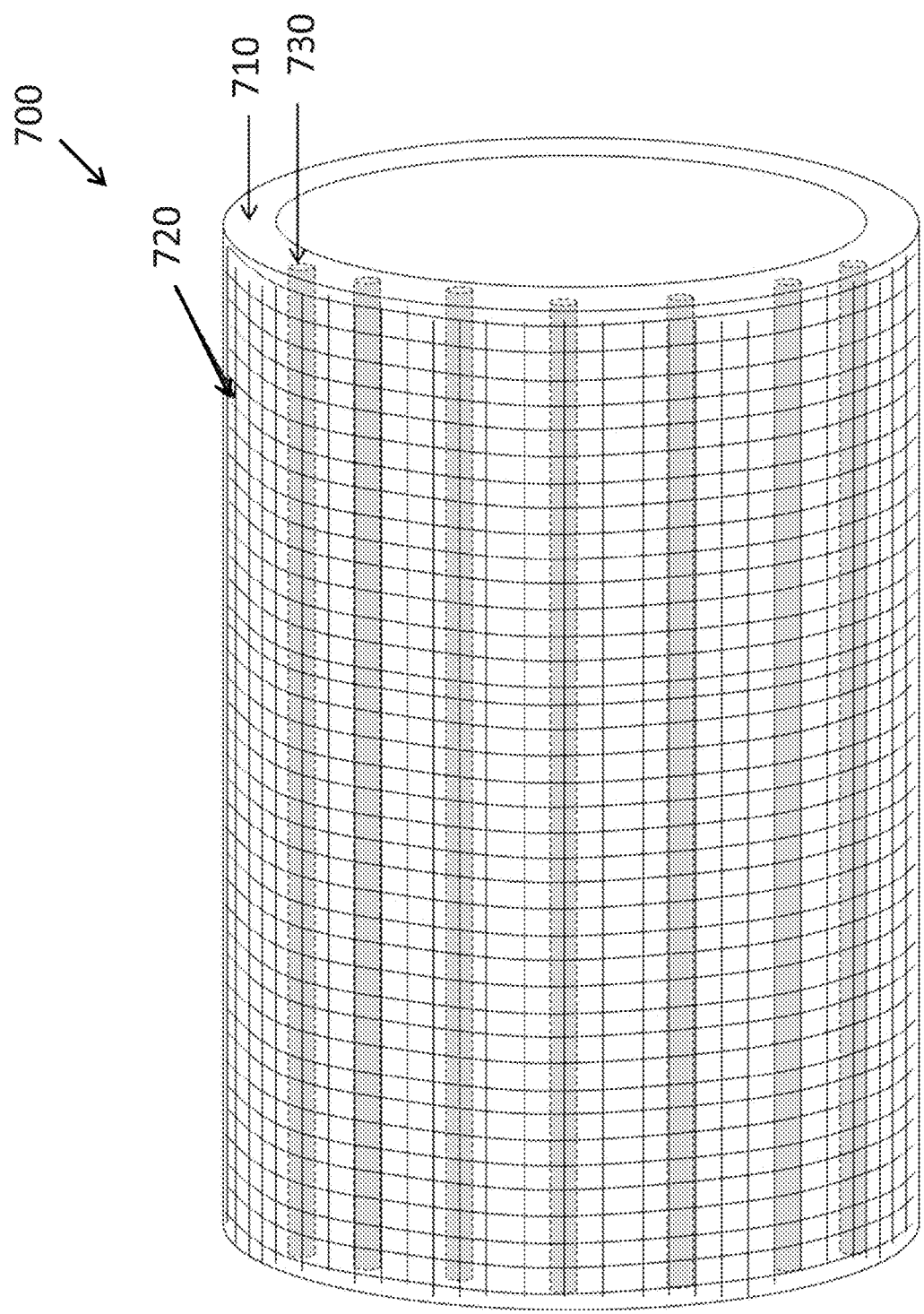
FIG. 7 is a high-level diagram illustrating an exemplary tube-shaped composite structure with structured parallel and perpendicular strips of fluorescent material and a two dimensional grating with two dimensional periodicity according to an embodiment of the invention.

A practical application of one or more of the disclosed embodiments is depicted in FIG. 7. As shown in FIG. 7, the periodically structured surface 720, or grating, is defined on the surface of a structural material 710, which is shaped to define an engineering structure such as a pipe 700. FIG. 7 further illustrates that the structural material 710 includes one or more fluorescent rods 730 embedded therein. Unlike the previously described exemplary embodiments, in this particular case, the surface 720 is curved instead of flat. However, the principles here generally remain the same as those described in relation to the previous exemplary embodiments. In use, perturbations in the material 710 would result in a modification of the diffraction pattern generated by the grating 720 on the emission of the fluorescent rods 730.

It should be noted that the components of the exemplary configuration shown in FIG. 7 are represented in a relative scale that the depicted composite structure 700 not necessarily to scale or accurate to practical implementations. In particular, the grating 720 is represented by a mesh of lines; this mesh of lines is intended to represent gratings similar to those described in relation to FIGS. 1-6B, or any two dimensional gratings, with periodically defined groves, spacing, or holes. In addition the relative distance between the lines in such a mesh is not representative of a practical distance between the grating's features with respect to the size of an object such as a pipe used, for example, in a pipeline. As mentioned above, the size of the features in the grating, or in the two dimensional photonic crystal arrangement, can be defined in view of the size of the perturbation to be revealed through inspection. Similarly, as shown in FIG. 7, the fluorescent material 730 is depicted as rods, however, it can be appreciated that the shape or arrangement of the fluorescent material within the composite structure does not necessarily have to be in rod form and the particular shape, size and orientation can be adapted to the geometry of the system and to the type of spatial information that is revealed by inspection. In the specific case of parallel fluorescent rods, as shown in FIG. 7, the diffraction pattern generated by inspection of a section of the pipe in a direction around the central axis would be similar to the one depicted in FIG. 6B.

As previously noted, the periodicity or dimensionality, of the grating can be larger than two (2). In the preceding exemplary configurations, only two-dimensional gratings were depicted: either two dimensional gratings with one dimensional periodicity, such as the ones of FIGS. 1, 2, 5A-5B, 6A-6B; or two dimensional gratings with two dimensional periodicity, such as the ones of FIGS. 3, 4, 7. Additional exemplary configurations of composite structures that are constructed to include three-dimensional gratings, with three-dimensional periodicity, also known as three dimensional photonic crystals are further described herein.

Figure 8A:
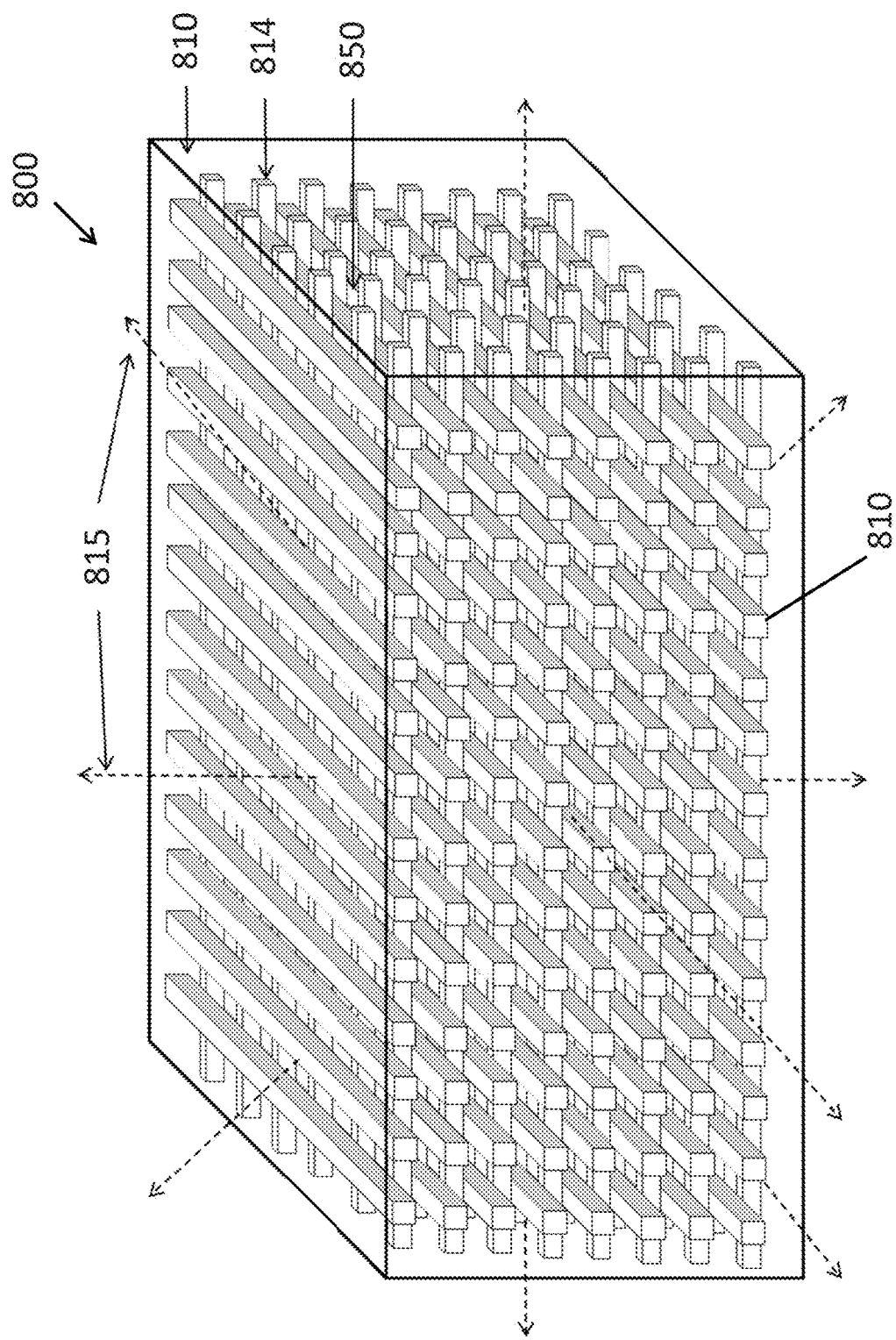
FIG. 8A is a high-level diagram illustrating an exemplary composite structure including rods defining a three dimensional photonic crystal as a grating according to an embodiment of the invention.
Figure 8B:
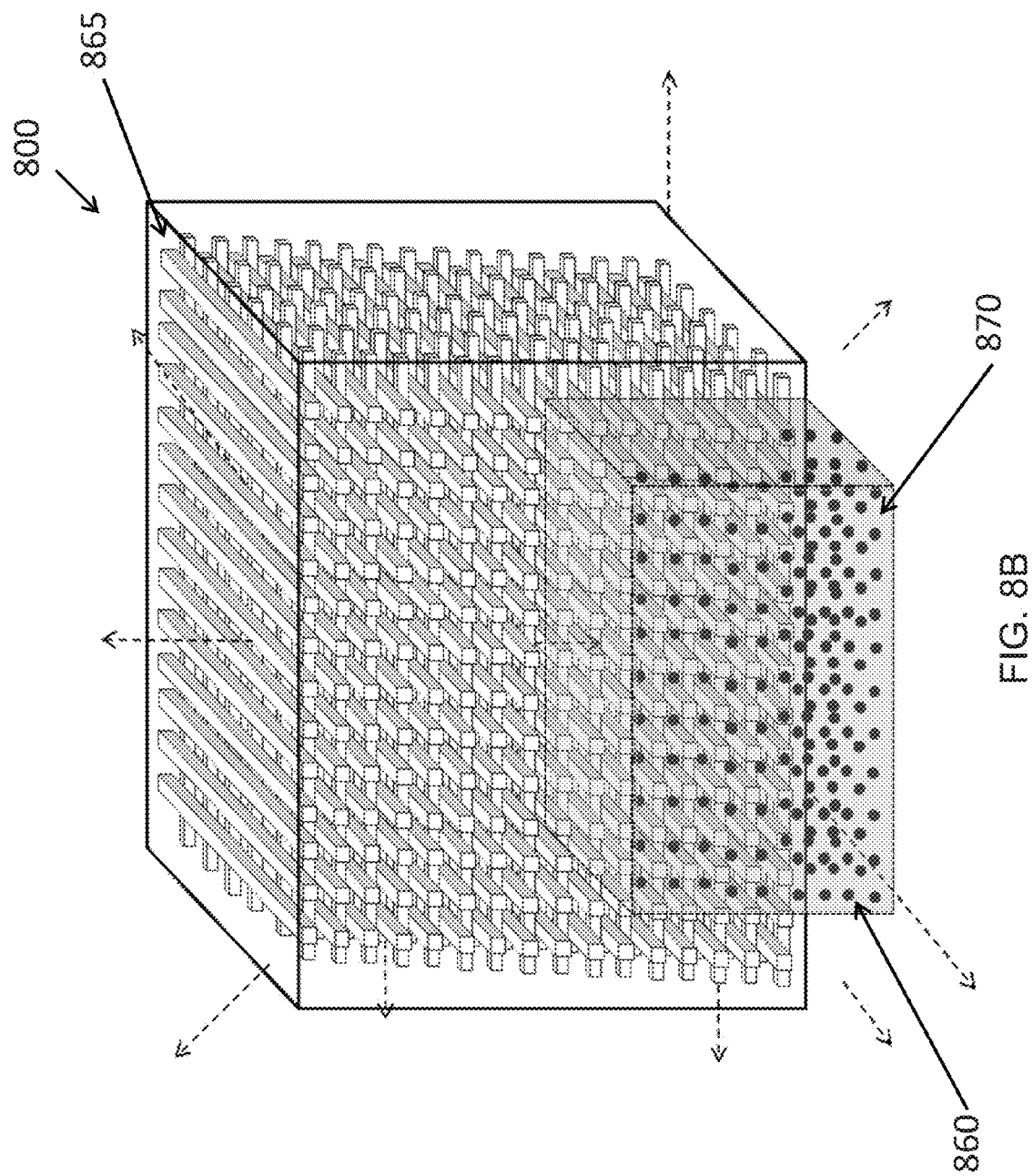
FIG. 8B is a high-level diagram illustrating an exemplary composite structure including rods defining a three dimensional photonic crystal as a grating according to an embodiment of the invention.

FIG. 8A-8B depicts an exemplary composite structure 800 constructed in accordance with one or more of the disclosed embodiments to include a rod like three dimensional photonic crystal as a grating, or diffraction element. The photonic crystal represented in FIG. 8A-B is comprised of rods of material 814, having a square cross section, distributed in such a way that they form a three-dimensional periodic lattice. It can be appreciated that elongate "rods" having alternative three dimensional shapes can be implemented as well. The structural material 810 can be a support for the lattice with a different refractive index. However, in some implementations, the material can be absent if the lattice can support itself, and if the lattice is coupled to a structural material in its proximity so as to detect the perturbation in the material in its proximity.

The exemplary lattice can be functional by itself without the addition of a fluorophore, as it would be responsive to an inspecting radiation creating regions of allowed bands and forbidden gaps according to a combination of Snell's law of refraction and Bragg's law of diffraction, as explained in the theory of photonic crystals and would be appreciated by those in the art. By monitoring the energy and angular distribution of these band structures it is possible to quantify perturbations of the material, as such perturbations would change the periodicity of the lattice and thus the conditions for diffraction and refraction.

However, similarly to the previously described embodiments including two dimensional lattices, one or more fluorophores can be added within the structure so as to facilitate more easy detection of the changes on the diffraction pattern caused by the three dimensional lattice on the emitting fluorophore or fluorophores. Such a fluorophore or fluorophores can be added inside the volume 850 of the three dimensional lattice, as shown in FIG. 8A, or on the opposite side with respect to the observer.

If the fluorophore or fluorophores are added inside the photonic crystal lattice, its distribution can be random given that, preferably, it is below at least 10 photonic crystal lattice planes counted from the observer. FIG. 8B shows a section of the exemplary structure 800 embodiment depicted in FIG. 8A with possible locations of the fluorescent elements indicated as black circles 860. The top side 865 of the structure shown in FIG. 8B is the one facing the observer. It can be appreciated that the scale in the figure is not accurate and the relative sizes of fluorophores and lattice elements are chosen only for the sake of clarity. In practical implementations, the size of the individual fluorescent elements can be orders of magnitude smaller than the lattice planes. Also the number of fluorescent elements is not necessarily representative of a real case, as the fluorophore or fluorophores can be also uniformly distributed throughout a portion of the structure 800 below the grating or within the grating, occupying a volume approximately identified by the shaded area 870 in FIG. 8B.

As shown in FIG. 8B, the volume 870 that can be occupied by the fluorophore or fluorophores can also extend well below the photonic structure, on the opposite side of the observer. As a result, the effect of the lattice on the emission radiation of the one or more fluorophores is the formation of diffraction lines represented as dashed arrows in FIGS. 8A and B, e.g., 815. Such diffraction lines are similar to the ones observed in X-ray diffraction for crystalline materials. In fact, from a physical point of view, the lattice 800 behaves like a crystal. The difference is the presence of one or more fluorophores, and that the size of this lattice and the material properties that relate to inspection wavelength can be defined according to the application. Accordingly, as a function of the exemplary lattice structure and construction and by monitoring the position, presence, or absence of these diffraction lines, it is possible to measure information regarding the perturbation affecting the material.

It can be appreciated that the particular geometry of the three dimensional lattice does not have to be necessarily the one shown in FIG. 8A-8B. For instance and without limitation, the lattice can be constituted by a three dimensional periodic distribution of beads, as depicted in FIG. 9, or of a material including a three dimensional distribution of holes therein, as represented in FIG. 10.

Figure 9:
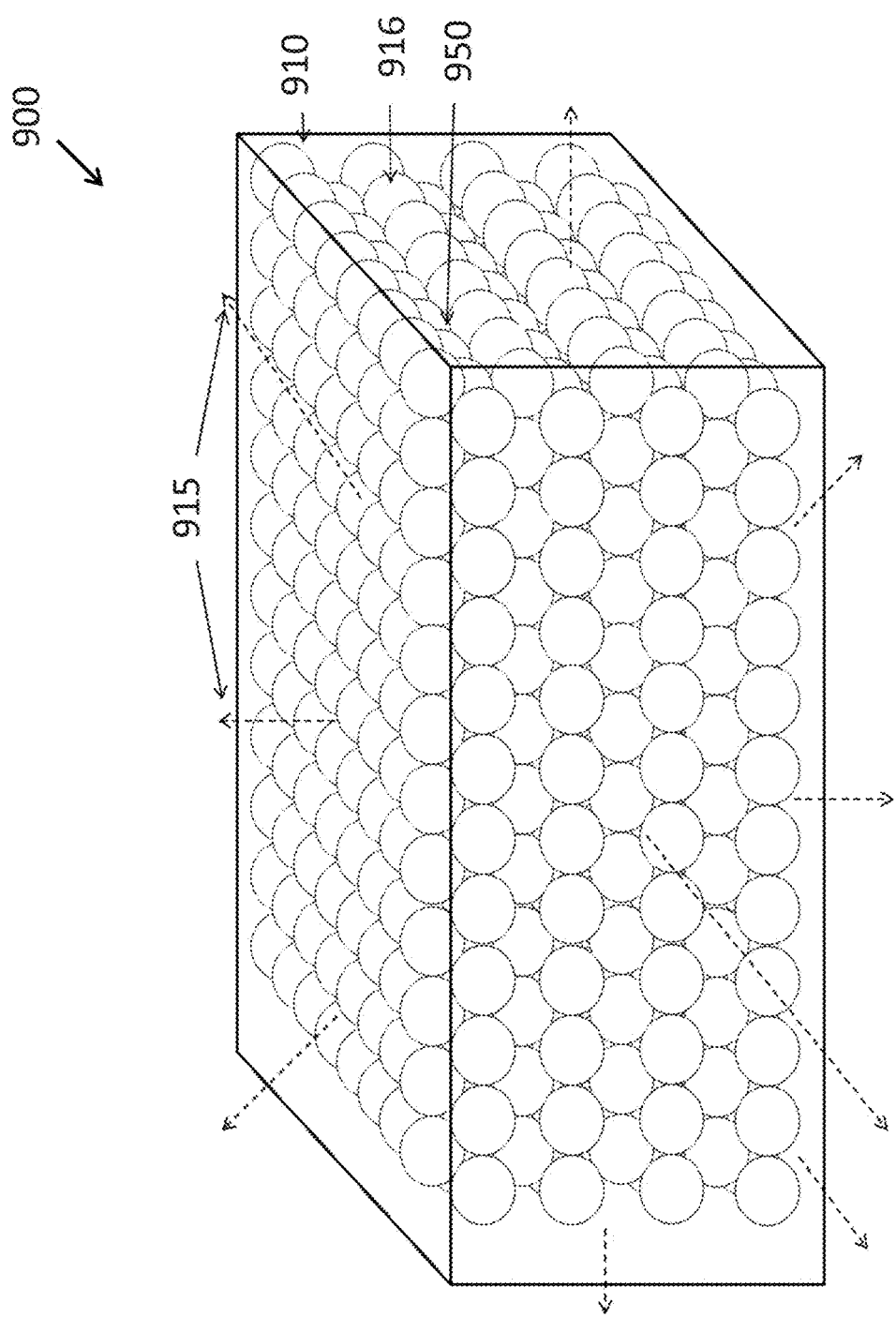
FIG. 9 is a high-level diagram illustrating an exemplary composite structure including beads defining a three dimensional photonic crystal as a grating according to an embodiment of the invention.

The photonic crystal 900 depicted in FIG. 9 has similar functionalities as the exemplary photonic crystal 800 shown in FIG. 8A-8B, however, the lattice is defined by a periodic distribution of beads 916 within a supporting material 910. The supporting material 910 can support the lattice and can have a different refractive index. In this exemplary embodiment, a one or more fluorophores can be contained within the volume 950 of the periodic lattice disposed within the supporting material 910. Regarding the location and distribution of the fluorophore or fluorophores similar considerations as for the embodiment of FIGS. 8A and 8B are valid also for the configurations depicted in FIGS. 9 and 10. One difference of this exemplary configuration is that the beads 916 themselves could be configured as fluorophores. For instance, the beads can be luminescent nano-particles, quantum-dots, or micro-particles activated with a fluorophore added as a dopant. In addition or alternatively, the fluorophore can be a filler in between the gaps formed by the lattice of beads 916. The inspection and analysis can be done in the same way as described for the embodiment depicted in FIG. 8A-8B. As a result of the exemplary lattice structure, the effect of the lattice on the emission radiation of the fluorophore or fluorophores is the formation of diffraction lines or directional forbidden gaps (or stop bands) represented as dashed arrows in FIG. 9, e.g., 915.

Figure 10:
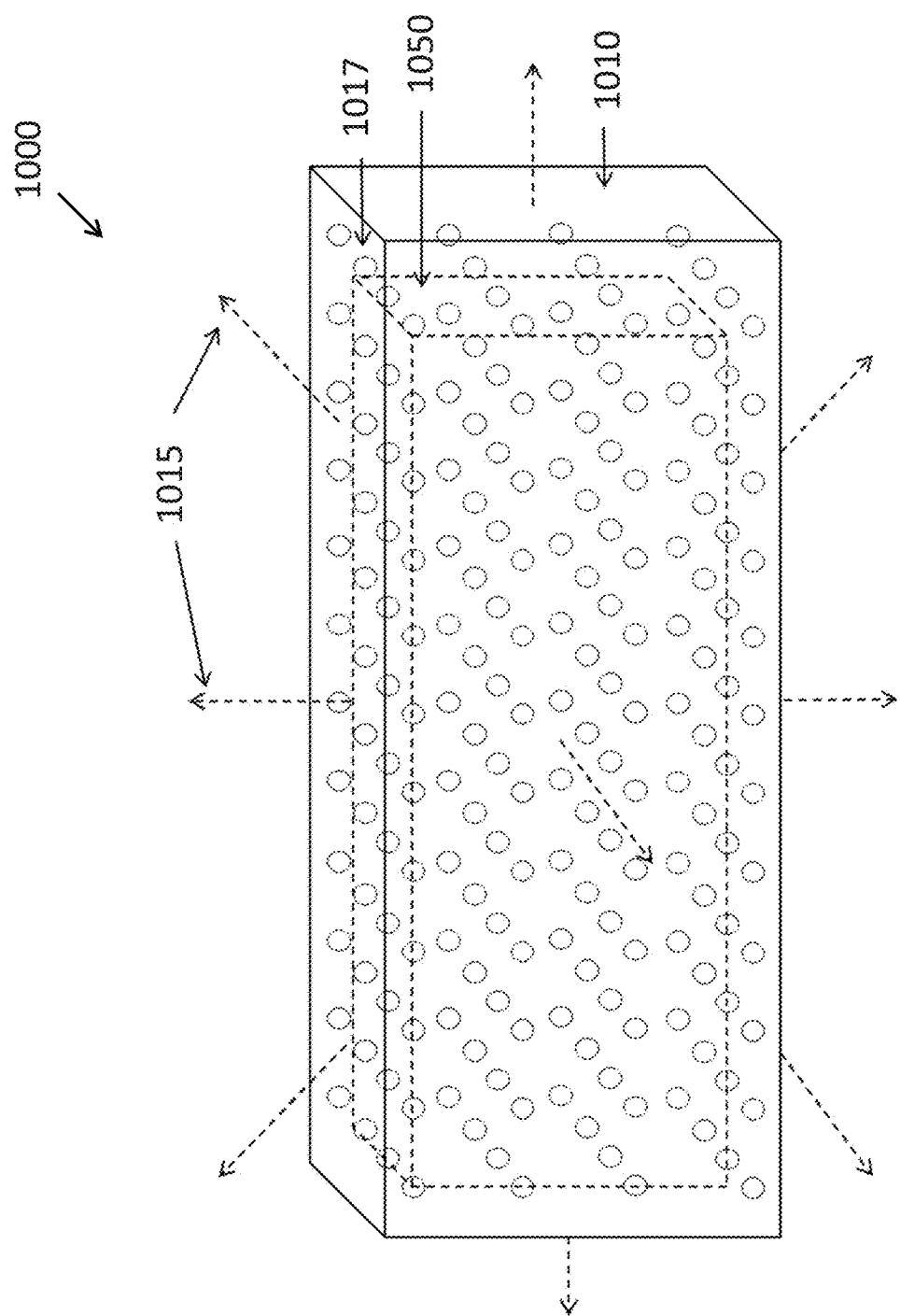
FIG. 10 is a high-level diagram illustrating an exemplary composite structure including voids defining a three dimensional grating and a one or more fluorophore materials according to an embodiment of the invention.

FIG. 10 depicts another exemplary configuration of a photonic crystal 1000. As shown, the crystal 1000 includes a three dimensional lattice that is formed by a periodic distribution of holes 1016 formed within a supporting material 1010. Such holes, however, in some implementations do not necessarily have to be holes, and they can be regions of a material with a different refractive index than material 1010. Material 1010 in this case is necessary as a support.

In FIG. 10 the volume/region within the material 1010 that includes the fluorophore or fluorophores is identified by the dotted volume 1050. The vicinity of the dotted volume to the surface of the material with respect to the number of photonic lattice planes identified by the periodic elements is not to scale and representative of a real device. The functionality of this particular configuration is also similar to the embodiments described in relation to FIGS. 8A-8B and 9. By monitoring the position of the diffraction lines 1015 it is possible to gain information about the perturbations affecting the lattice, which is, in turn, a function of the perturbations affecting the constituent materials.

The types of perturbations that are detectable as a function of the exemplary photonic crystals that are constructed in accordance with one or more of the disclosed embodiments, are not limited to physical deformation and can also include temperature changes and changes in the chemical composition, liquid absorption, or functionalization of the composite structures. While these changes might not modify the spacing between the periodic features of the grating, they can cause a change in refractive index. In turn such a change will modify the diffraction pattern by modifying the angle of refraction and, thus, the directions of diffraction. In the exemplary configurations that do not include a fluorophore, such material changes can cause a change of wavelength for a specific angle of observation. In the exemplary configurations that include one or more fluorophores, the material changes can cause a change in the angle between the diffraction directions and thus a change in the spacing between the diffraction lines.

The distinction between a physical change and a change in temperature or in chemical composition is strait forward, because a physical change is generally localized on a small portion of the object, while the rest are delocalized over larger areas. Nevertheless, there could be instances in which different types of perturbations affect the same areas; in this case it the different types of perturbations can be distinguished by comparatively analyzing a reference material without a grating to detect any change in refractive index associated with changes in chemical composition or temperature.

Once this correspondence between deformation and optical signal has been established, the detection system can be used to quantify one in terms of the other. More specifically, as explained above the detection device can be used to reveal and quantify the perturbation in terms of the optical signal. Conversely, it can be used to reveal and quantify the change in wavelength or in diffraction angle as a material deformation.

Figure 11B:
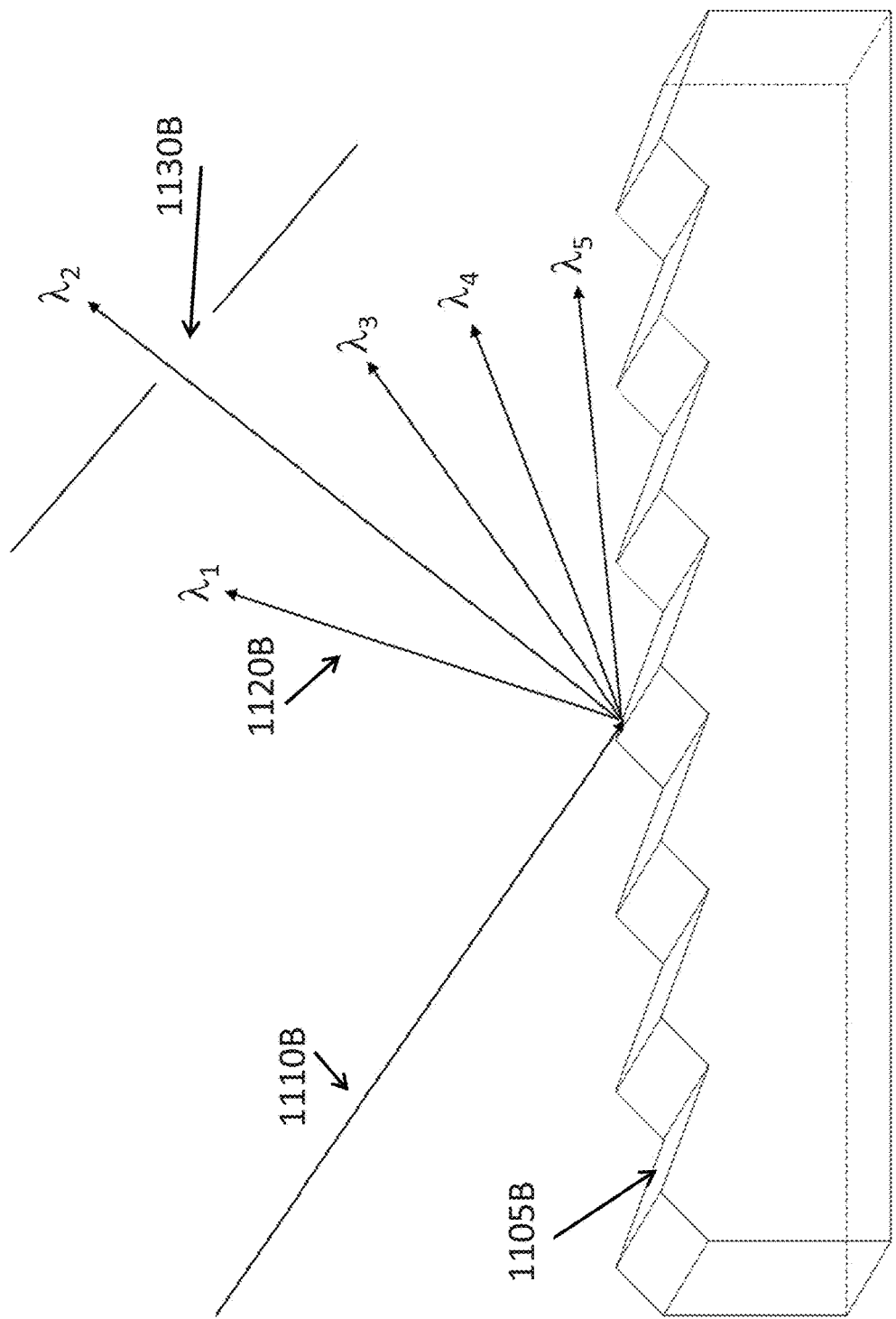
FIG. 11B is a high-level diagram illustrating the exemplary configuration of the monochromator of FIG. 11A utilizing a stretchable diffraction grating in stretch conditions as a wavelength selection mechanism.

Under the same principles of operation disclosed herein for constructing composite materials and detecting perturbations in materials, in some exemplary embodiments, an inspection device can be inversely calibrated to control and select a known band of wavelengths. More specifically the control and selection of a known band of wavelength can be performed as a function of pressure that is applied on a material, or of any deformation to which the material is subject. This application can provide the optical dispersive element required in a monochromator or spectrometer wherein the principle of operation is based on a linear stress either in compression or in extension and does not require a rotation. Usually, a monochromator is constituted of a grating coupled with a slit: the grating divides the radiation, into its different wavelengths at different angles. The slit positioned at a certain distance from the grating only lets one wavelength through. In order to change the wavelength that passes through the slit the grating is rotated so that a different diffraction angle is directed toward the slit. By applying a photonic structure as here described or a grating to a stretchable polymer or material, the wavelength selection can be performed by varying the spacing of the periodic structure rather than the angle of observation. Accordingly, in this configuration it is not necessary to rotate the grating to change the wavelength. An exemplary configuration of the photonic structure used in a monochromator to provide this complementary application of the technology is depicted in FIGS. 11A and 11B. FIG. 11A depicts an exemplary photonic structure 1100 constructed in accordance with the disclosed embodiments in the situation where the incident white light 1110 (or more in general a radiation containing multiple wavelengths) is reflected and diffracted by the photonic structure 1100 having a grating surface 1105 that, in this example, is not deformed. The different wavelengths 1120 emerge thus at different angles, and only a limited portion of them are able to pass through the monochromator slit 1130. FIG. 11B represents the structure 1100 (shown as 1100B) in the situation in which the photonic element or the grating 1130B is stretched (e.g., from stress applied to the structure), and, as such, the spacing of the periodic features of the grating is increased and thus the diffraction pattern 1120B changes. As a result the wavelength that emerges from the slit 1130B will be different from the previous one (e.g., the relaxed photonic structure). In this way it is possible to achieve the same wavelength selection performed by a monochromator, but with a linear system based on compression or extension of the photonic structure used in the monochromator. Therefore, if, for example, the grating material used in the monochromator is a soft polymer such as PDMS, the wavelength selection can be performed by applying pressure on it or a tensile force.

The possible methods of fabrication utilized for the above mentioned embodiments can be many. Depositions of materials constituting different layers depicted in FIGS. 1 to 6 can be performed by spin coating, drop casting, Sputtering, Physical Vapor Deposition, Chemical Vapor Deposition, Molecular beam epitaxy, and the like. The structuring of the composite structure to obtain a 2 dimensional photonic crystal either with 1D or 2D periodicity, can be also achieved in many different ways depending on the application and on the size of the periodicity desired. One possibility is to use laser interference lithography, to impress a pattern on a photoresist layer and successively etch it on the substrate. Another possibility is to use a mask to generate the desired pattern also on a photoresist layer. Both these systems provide the ability to achieve a size of the periodicity of below the micrometer. For smaller scales, the structuring can be done by electron beam lithography or stencil lithography. Another common way to fabricate a diffraction grating is by ruling the pattern using a ruling engine. For larger scale applications, it is possible to use molding techniques, such as injection molding, hot embossing, and the like.

Furthermore, when the photonic material only works in reflection and no transmission is required, the interface between the two materials with different refractive index can be enhanced with the deposition of a reflective layer, such as Aluminum, Copper, Chromium, Gold, and the like.

The fluorophore or fluorophores can also be introduced into the composite structure in many different ways: for example a fluorophore that is soluble in the polymer can be simply mixed into the polymer before curing: either in the elastomer or in the curing agent. For instance the fluorophore fluorescein can be dissolved in a variety of epoxy polymers by dissolving it into the elastomeric portion before curing, and then curing it at room temperature. Another example could be the utilization of metal nanoparticles such as Silver or Gold as fluorophores. These can be stabilized with the opportune ligand such as benzoate and then dispersed into the curing agent of a Polydimethylsiloxane (PDMS) such as the curing agent of the Sylgard 184 polymer kit of Dow Corning.

In case sharper emission transitions are required, then lanthanide ions can be introduced as dopants in a polymer, a glass, or in a crystalline lattice. In case they need to be introduced into a polymer, they can be stabilized in it as complex as a coordination compound, while, if they need to be introduced into a glass or crystal, they can be added in ionic form during growth: for example, the oxides of the lanthanides can be added to the mixture of oxides forming the crystal before the start of a crystal growth technique, such as for example the flux growth. Other possible techniques to grow doped crystals include Czochralski, Hydrothermal growth, and the like.

In the case the fluorescent layer is not continuous like in FIGS. 1, 2, 3 and 4, but it presents a discreet structure, such a structured deposition can be achieved with one of the lithographic techniques described above for the fabrication of the photonic structure. For example, after a substrate has been etched through a photoresist a fluorophore can be added to the substrate, before the removal of the photoresist.

The embodiments represented in FIG. 8A can also be fabricated in a similar manner alternatively etching and filling perpendicularly oriented features on a substrate.

If these composite structures are sized above the micro scale, in case the system is designed to interact with long wavelength radiations, such as micro- or radio-waves, the fabrication methods are generally simpler than below the micro scale and can be achieved with conventional molding, or rapid prototyping processes.

For the fabrication of a three dimensional photonic structure such as the one depicted in FIG. 9 there is also a variety of techniques that can be utilized. For the nano and micro scale, a simple technique is self-assembly. For example Silica, Polystyrene, or Poly(methyl methacrylate) (PMMA) beads can self-organize themselves in a vertical or horizontal deposition technique from the slow evaporation of a dispersion of the beads. An alternative way is to form photonic crystal by shear-based nano-assembly of beads in polymers.

Inspection Device

In accordance with one or more of the disclosed embodiments, various exemplary systems and methods for non-destructive inspection of structures to detect and quantify perturbations are further described herein.

In some implementations, the inspection device can be used to analyze the response of a photonic material to perturbations such as tensile stress, compressive stress, bending, deformation, changes in temperature, in chemical composition, and in refractive index. Although the exemplary inspection device can be used independent of the exemplary composite structures that were previously described in relation to FIGS. 1-10, the exemplary systems and methods for non-destructive inspection are further described herein in relation to the previously described composite structures.

More specifically, the inspection device is configured to emit an inspecting radiation into the material being inspected. As noted above, the composite structures previously described consist of a photonic material whose periodicity can be affected by perturbations in its surrounding. Such periodicity change results in a change in the diffraction pattern or photonic band structure generated by such a periodic lattice. It can be appreciated that the lattice can be mono-, two-, or three-dimensional. The inspection device is further configured to measure characteristics of the resulting diffraction pattern and, accordingly, measure the change in the diffraction pattern relative to an expected pattern.

Moreover the inspection device is configured to use, as an input, the change in the diffraction pattern and provide, as an output, a quantification of the perturbation affecting the material. In particular, the inspection device is configured to transform the wavelength and the angle information about the diffracted radiation into a measure of displacement. The inspection device consists of one or two components together utilizing two similar principles to achieve such a transformation. One component transforms the wavelength information into a displacement, while the other component transforms the angular information into a displacement. The periodic structure being inspected considered could be for example the composite structure including a diffraction grating such as the one described in relation to FIG. 2.

According to a salient aspect, the inspection device is configured to quantify deformations in photonic materials through a wavelength change, or a diffraction angle change quantified from an intensity variation. As a result, the inspection device provides the ability to detect perturbations with a sensitivity that is tunable through the choice of the inspecting wavelength and the corresponding periodicity of the photonic material. Moreover, the inspection device provides a multi-dimensional level of sensitivity.

The system comprising the photonic material and the inspection device is tunable to the size of deformation or defect that needs to be detected. For example, if the user is interested in detecting defects on the order of few hundreds of nanometers, the distance between the periodic features in the photonic structure needs to be at least on sub-micron scale. If the spacing is well above the micro scale, deformations on the order of 100 nm might go unnoticed. While if the spacing is on the order of tens of nanometers, the sensitivity will be for defects of similar scale and thus suitable to detect the defects of interest but not required, because over sensitive.

At the same time the inspecting radiation utilized in the inspection device and the range of sensitivity of the device needs to be able to interact with the features of the material. Therefore, for a sensitivity on the nanometer scale the radiation of the device needs to include the visible range of the electromagnetic spectrum, and the sensor needs to be sensitive to the same range. For the detection of larger scale defects, for example millimeters, the spacing of the periodic features in the materials can be on the millimeter to the submillimeter range and thus it is sufficient for the inspecting radiation of the device to include infrared to microwave wavelengths.

The multidimensionality of the sensitivity is determined also by the configuration of the photonic material and the inspecting device. For example, for embodiments of the photonic materials with two dimensional periodicity such as the ones depicted in FIGS. 4, 6, and 7 an anisotropic deformation of the material that is larger along one axis (for example in FIG. 4 the axis perpendicular to the plane of the page) than along the other axis (in FIG. 4 the axis on the plane of the page) will result in the diffraction angles caused by the features along the first axis to be larger than the ones caused by the feature along the latter axis. Therefore the spots 465 on the top surface of FIG. 4 that are aligned perpendicular to the plane of the page will be farther from each other than the ones aligned along directions parallel to the plane of the page.

This two dimensional sensitivity that can be observed by naked eye from the embodiment in FIG. 4 can be also quantified by the inspection device. For example this change in the spacing between the diffraction lines can be observed in an image captured by the camera sensor in the device 1260, or as a directional intensity change measured by the CCD array 1214.

Turning briefly to the exemplary composite structure depicted in FIG. 2, the grating 220 is responsible for the diffraction, while the layer 250 is fluorescent. While one or more fluorophores can be incorporated to enhance the detection of perturbations, it is not essential to the operation of the exemplary inspection device. In fact, a grating responds to a white light source, by decomposing it into all different wavelengths; while it responds to a laser beam by diffracting it into separate beams emerging from the grating at different angles depending on the diffraction order, which is indicated in figure as m. Accordingly, the inspection device can be configured to emit one or more electromagnetic radiation sources including a diffused radiation source (such as a white light source) and a laser so as to be useable with a variety of different composite structure configurations (e.g., irrespective of whether the structure includes a fluorophore).

Once the material is exposed to a white light source, such as the one coming from an LED lamp, a diffraction pattern will be generated with different wavelengths or colors being reflected and diffracted at different angles. Each one of these wavelength for a specific angle of observation is related to the spacing between the periodic features of the grating according to the Grating Equation:

$$n\lambda = d(\sin \beta - \sin \alpha) \quad (1)$$

In case of a reflection grating or;

$$n\lambda = d(\sin \beta + \sin \alpha) \quad (2)$$

In case of a transmission grating, if for example the radiation diffracted comes from a fluorescent layer located on the opposite side of the gating with respect to the observer (as represented in FIG. 2), or if the inspection radiation simply hits the grating on the opposite side with respect to the observer.

In equations (1) and (2) n is an integer number indicating the integer number of wavelengths, $\lambda$ is the wavelength, d is the spacing between two adjacent periodic features, a is the angle of incidence, $\beta$ is the angle of reflection, which coincides with the diffraction angle, when these equations are satisfied.

In normal conditions, if the sample is not deformed by a defect, the periodicity of the grating will be the same over the entire area, and it will thus generate a smooth diffraction pattern, in which, at any position, the wavelength is changing smoothly with the angle of observation; or, for a single point of observation, the angle is changing smoothly over the illuminated area, because different positions still correspond to different values of $\alpha$ and $\beta$. In the case of a defect, on the other hand, the change in wavelength (or color) in proximity and in correspondence to the defect will present an irregularity, as the periodicity of the grating will be locally modified. By knowing the angles of diffraction, which are related to the architecture of the device (described hereafter) and by measuring the wavelength, observed, by using equations (1) and (2) the inspection device can calculate the distance d between the periodic features and compare it to the unperturbed d (spacing), which is predefined for the sample. The angles of incidence are known based on the relative positions of the illuminating source and the observed spot on the material. The angles of diffractions are known by considering the relative position of the spot observed on the material and the sensor in the device, or the size of the periodicity of the photonic structure on the material. Alternatively, the same information can be derived from the distance between the radiation source and the sensor slit, and the distance of the device from the photonic material. All these are parameters that can be initialized, modified, or fixed for the specific device, and/or a specific material.

Nevertheless, even if the architecture of the device (relative position of radiation source and detector) and the size of the periodicity of the photonic structure is not considered or known. The observation of the wavelength or diffraction angle change, with or without device, will still allow a quantification of the perturbation or defect. The reason is that the information required is not necessarily the absolute value of displacement, but its relative change. Therefore, if throughout the analyzed area of material the displacement appears as a certain value and in a specific area appears as a different value, the more relevant information is the difference between these two values, rather that the absolute values. For these reasons, in certain cases it might not be necessary to consider all of the parameters mentioned above, but just the relative change. Conversely, if the knowledge of the exact value of displacement is required, all configuration parameters can be considered, or the value displaced can be calibrated with the known size of periodicity (if even the starting value of periodicity is not known, it can be measured with microscopic techniques).

Furthermore, if none of the above parameters are known or also the initial variation is too large and disordered (for example on a surface that is not smooth from the start) the quantification can be confirmed by comparing the diffraction pattern or the wavelength image (color image or photograph) with a reference image taken when the structure is applied or at a significant point in time.

If, instead of diffused radiation, the material is exposed to a laser beam, the laser beam will also be diffracted according to equations (1) and (2). The difference in this case is that the wavelength is constant and the diffraction conditions will be satisfied only at certain angles, resulting in an odd and symmetric distribution of diffracted beams. If the material is not perturbed, the angular difference between these diffracted beams will be the same throughout the material. However, if there is a deformation of the material, and thus of the periodicity of the grating, the diffraction angle between the beams will change. By monitoring this angle across the material it is possible to identify deformed regions, by calculating d from equations (1) and (2), knowing the $\lambda$, and measuring the angle.

Figure 12A:
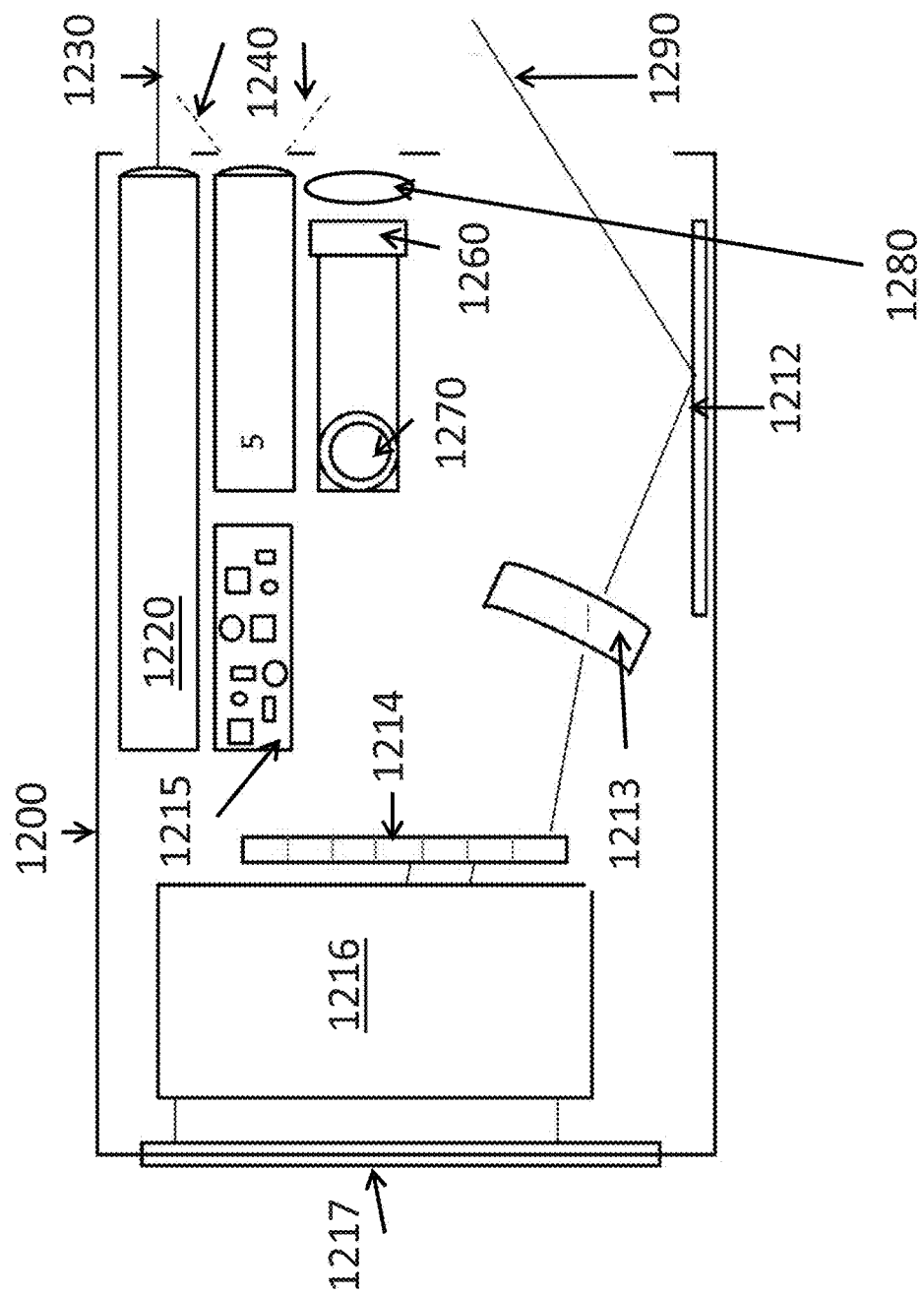
FIG. 12A is a high-level diagram illustrating a top view of an exemplary inspection device according to an embodiment of the invention.
Figure 12B:
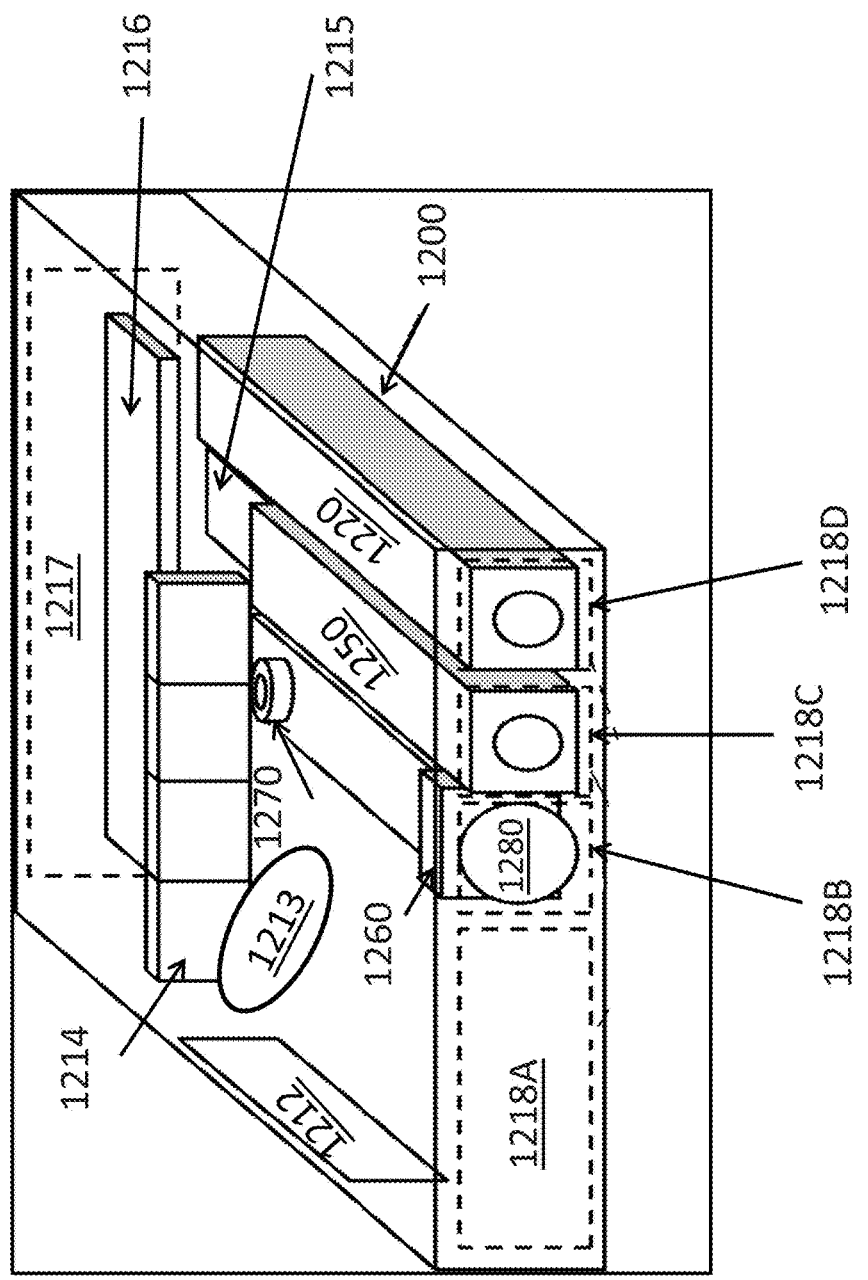
FIG. 12B is a high-level diagram illustrating a front perspective view of the exemplary inspection device of FIG. 12A according to an embodiment of the invention.
Figure 12C:
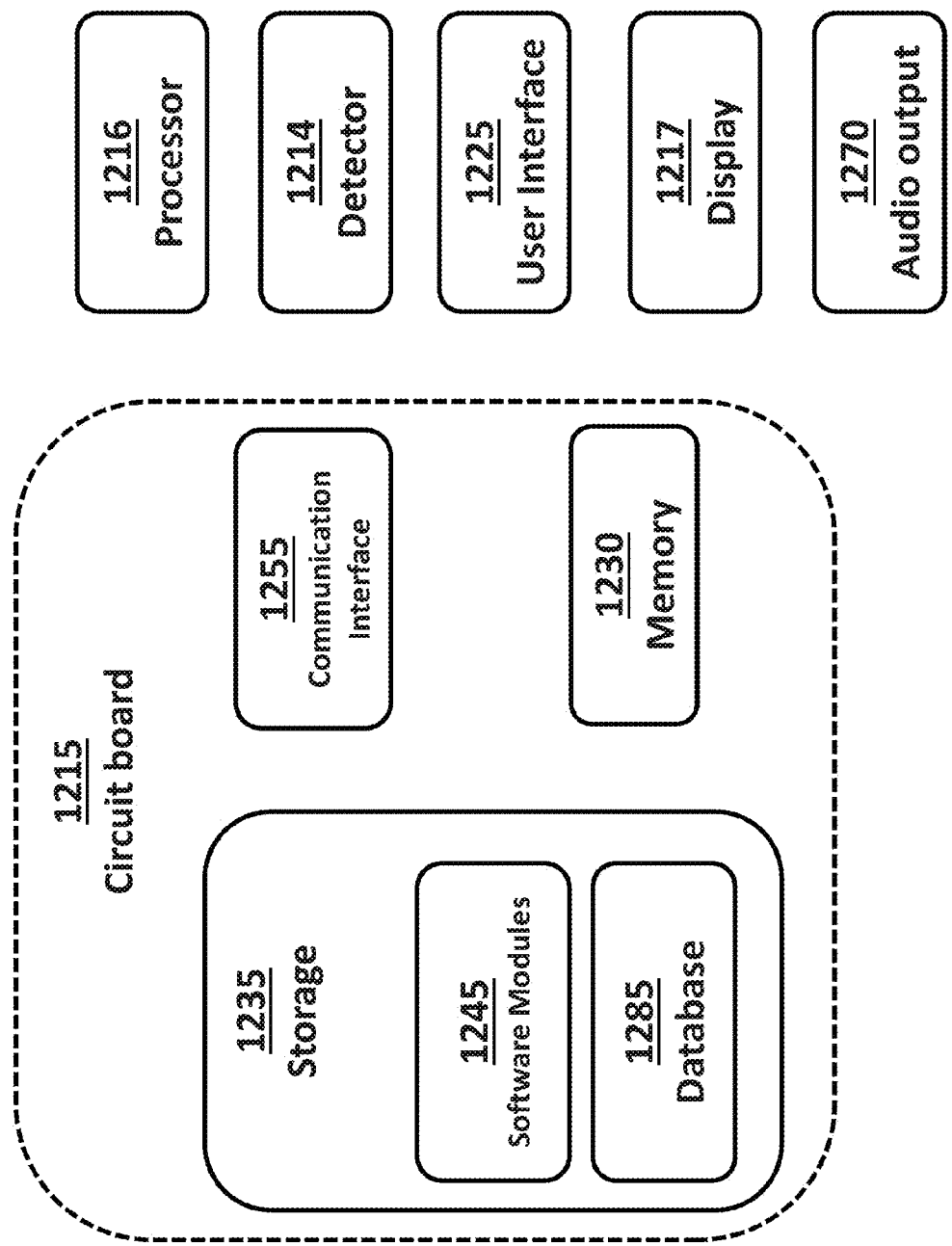
FIG. 12C is a block diagram illustrating exemplary configuration of computer hardware and software components of the inspection device of FIG. 12A according to an embodiment of the invention.

In view of the above considerations, a configuration of the basic components of an exemplary inspection device 1200 is further described herein in relation to FIGS. 12A-12C.

In the exemplary embodiment shown in FIG. 12A, the inspection device 1200 includes a laser 1220 and a diffused radiation source 1250, such as an LED white light source. Although source 1250 is described as a diffused electromagnetic radiation source, the source can also be configured to emit radiation with constant intensity over a certain range of wavelengths, this range could be broad, or it could be limited to a narrow range of wavelengths, it could be in the visible range or in any other range of the electromagnetic spectrum. Also shown is a lens 1280, for focusing the radiation emitted by the diffused radiation source 1250 and diffracted by a sample being inspected. The lens is configured to focus the diffracted radiation into a camera sensor 1260, which collects it and is further configured to provide the captured image to the processor 1216.

The inspection device can be arranged with various computer hardware and software components that serve to enable operation of the inspection device and, more specifically, perform operations relating to the analysis of the information captured by the detector 1214. FIG. 12C is a block diagram depicting these exemplary computer hardware and software components of the inspection device 1200 including, the processor 1216 and the circuit board 1215. As shown in FIG. 12C, the circuit board can also include a memory 1230, a communication interface 1255 and a computer readable storage medium 1235 that are accessible by the processor 1216. The circuit board and/or processor can also be coupled to the display 1217, for visually outputting information to the user, and a user interface 1225 for receiving user inputs and an audio output 1270 for providing audio feedback to a user as would be understood by those in the art: for example the device could emit a sound or a visual signal from the display or from a separate indicator light when a defect or deformation above a certain threshold is encountered. The threshold can be set manually or by default prior to the measurement through the user interface which could be a touch screen or opportune keyboard. Although the various components are depicted either independent from, or part of the circuit board 1215, it can be appreciated that the components can be arranged in various configurations.

The processor 1216 serves to execute software instructions that can be loaded into the memory. The processor can be a number of processors, a multi-processor core, or some other type of processor, depending on the particular implementation.

The memory 1230 and/or the storage 1235 are accessible by the processor 1216, thereby enabling the processor to receive and execute instructions stored on the memory and/or on the storage. The memory can be, for example, a random access memory (RAM) or any other suitable volatile or non-volatile computer readable storage medium. In addition, the memory can be fixed or removable. The storage can also take various forms, depending on the particular implementation. For example, the storage can contain one or more components or devices such as a hard drive, a flash memory, a rewritable optical disk, a rewritable magnetic tape, or some combination of the above. The storage also can be fixed or removable or remote such as cloud based data storage systems.

One or more software modules 1245 are encoded in the storage 1235 and/or in the memory 1230. The software modules can comprise one or more software programs or applications having computer program code or a set of instructions executed in the processor 1216. Such computer program code or instructions for carrying out operations and implementing aspects of the systems and methods disclosed herein can be written in any combination of one or more programming languages. The program code can execute entirely on HMI 105, as a standalone software package, partly on the HMI and partly on a remote computer/device (e.g., control computer 110) or entirely on such remote computers/devices. In the latter scenario, the remote computer systems can be connected to inspection device through any type of network, including a local area network (LAN) or a wide area network (WAN), or the connection can be made through an external computer (for example, through the Internet using an Internet Service Provider).

Included among the software modules 1245 is one or more analysis programs that can be executed by the processor 1216. During execution of the software modules, the processor is configured to perform various operations relating to the analysis of the radiation captured by the detector 1214 for detecting and quantify perturbations in the inspected materials as a function of the diffraction pattern, as will be described in greater detail below. It can also be said that the program code of the software modules 1245 and one or more of the non-transitory computer readable storage devices (such as the memory 1230 and/or the storage 1235) form a computer program product that can be manufactured and/or distributed in accordance with the present disclosure, as is known to those of ordinary skill in the art.

In addition, it should be noted that other information and/or data relevant to the operation of the present systems and methods can also be stored on the storage 1235. For instance, the database 1285 can include prescribed settings and parameters that relate to the various materials and structures that can be inspected using the inspection device such as expected diffraction patterns, characteristics of the materials any periodic gratings (e.g., orientation, period, spacing of features, optical parameters, transmission wavelength, etc.) or characteristics of any fluorophore present in the material (e.g., excitation wavelength and emitted radiation wavelength) and the like, as will be discussed in greater detail below. Similarly, the database can store other operational parameters that are specific to the inspection device and various modes of operation (e.g., diffused radiation based inspection and laser-based inspection). It should be noted that although storage 1285 is depicted as being configured locally to the storage of the inspection device, in certain implementations, database and/or various of the data elements stored therein can be located remotely (such as on a remote computer or networked server—not shown) and connected to the inspection device through a network in a manner known to those of ordinary skill in the art. It can also be appreciated that the board 1215 can also include or be coupled to a power source (not shown) source for powering the inspection device.

A communication interface 1255 can also be operatively connected to the processor 1216 and can be any interface that enables communication between the inspection device and external devices, machines and/or elements such as a control computer or a networked server (not shown). The communication interface includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting the inspection device to other computing devices and/or communication networks, such as private networks and the Internet. Such connections can include a wired connection or a wireless connection (e.g., using the IEEE 802.11 standard) though it should be understood that communication interface can be practically any interface that enables communication to/from the inspection device.

Returning to FIG. 12A, in some implementations, the inspection device 1200 can be configured to use the diffused radiation source 1250 to perform a preliminary analysis of the sample to identify an area of the sample presenting a deformation. Moreover, the inspection device can be further configured to use the laser source 1220 to perform a more detailed analysis of the identified area and to obtain a quantitative measurement of the deformation. However, it can be appreciated that the inspection device could consist only of one of these two radiation sources and provide reliable results. For instance, the wavelength analysis performed using the diffused radiation source could also provide quantitative information as to the extent of the perturbation, as described above.

In particular, the diffused radiation source 1250 is configured to emit a cone of radiation 1240 (delimited by the dotted lines in FIG. 12A). The photonic material, in response to this radiation (such as white light for example), will generate a pattern of diffraction by reflecting and diffracting different wavelengths along different directions. This diffraction pattern will be focused through the lens 1280 into the camera sensor 1260, which collects it and provides the captured image to the processor 1216 for further analysis.

In case of a local perturbation the angular variation of wavelength will not change as uniformly as in absence of perturbation. This abrupt change in color can be recognized by the processor 1216, which is configured by executing one or more of the software modules including the analysis software program. The processor can be further configured to generate a notification accordingly. For instance, based on the gradient of the color change in the captured image, the processor can transmit an alert signal such as a sound through an audio or light emitter 1270. The processor can be further configured by executing the analysis software to analyze the abrupt color variation identified by the system. Moreover, the processor can be configured to associate a periodicity size to the specific wavelength measured (as described above), and obtain the size of the perturbation by comparing it to a reference such as the regular size of the periodicity measured in the unperturbed areas.

Figure 13A:
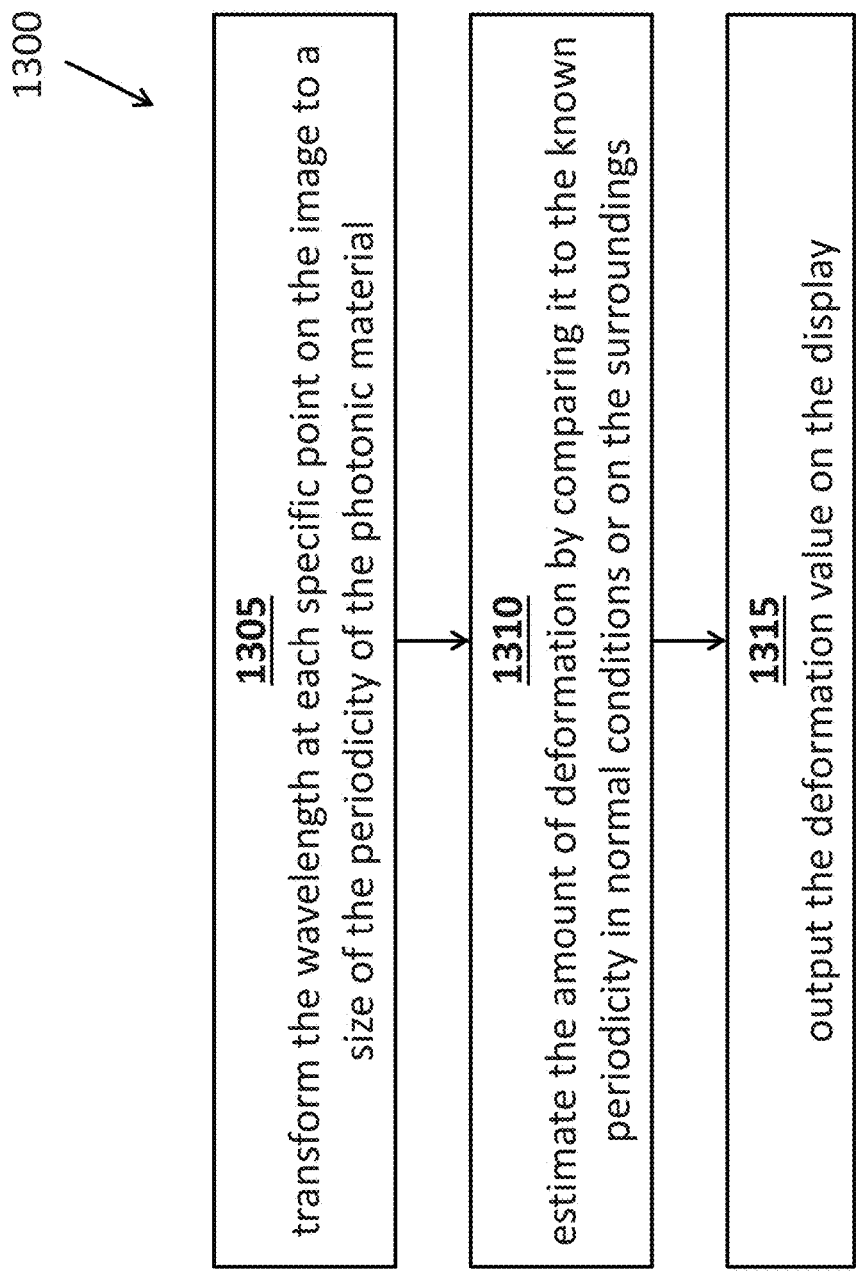
FIG. 13A is a flow diagram illustrating a routine for computing deformation of a photonic structure according to an embodiment of the invention.

FIG. 13A illustrates an exemplary routine 1300 for analyzing the color variation to determine a periodicity size for the specific wavelength measured with continued reference to the inspection device 1200 of FIGS. 12A-12C. In particular, at step 1305, the processor 1216, which is configured by executing one or more of the software modules 1245 including, the analysis software program, transforms the wavelength at each specific point on the captured image to a size of the periodicity of the photonic material. As explained above, the transformation can be performed as a function of the geometry of the device and the specific diffraction angle corresponding to the specific wavelength spot analyzed. Once the size of the periodicity has been determined, the configured processor can, at step 1310, compute the amount of deformation, by comparing it to the known periodicity in normal conditions. In addition or alternatively the periodicity can be compared relative to the determined periodicity of the surroundings, for instance, to identify any differential that exceeds a prescribed threshold. Then at step 1315, the configured processor can, using the calculated deformation value, output the results on a display 1217 that is coupled to the processor. Furthermore, at step 1315, the complete image, or wavelength map can be output by the configured processor using the display 1217. In addition, the information can be stored by the processor in the storage 1235 and/or sent via the communications interface 1255 to a computing device or over a network to a centralized processing center server (not shown) for further analysis and/or storage. FIG. 11 depicts two side-by-side visual images of the wavelength map generated and output by the inspection device for a sample being inspected. In particular, on the left side of the image, the map is shown without stress applied to the sample and, on the right side of the image, the map of the sample is shown while stress is applied to the sample.

An alternative method for detecting and analyzing perturbations of the sample material is based on the diffraction of the laser beam 1230. As shown in FIG. 12A, the incoming beam 1290 is the diffracted beam resulting from the interaction of the emitted laser beam 1230 with the photonic sample material. This beam 1290 can be detected by a detector 1214, and its position on the detector will be indicative of the diffraction angle, which is related to the size of the periodicity of the photonic material according to equation (1) above. In FIG. 12 there are two extra elements depicted including a mirror 1212 and a lens or an optical filter 1213 to modulate the intensity of the beam. Both these elements are not required for the basic functioning of the inspection device 1200, however, they can be beneficial in that they can provide a more efficient measurement. In particular, the presence of the mirror 1212 can extend the optical path and direct the beam to the location of the detector, which can be defined with the goal of minimizing the size of the device, for example. Moreover, the inspection device 1200 can be configured to include more than one mirror for this purpose.

The function of element 1213 could be one or more of, a filter to reduce the intensity of the laser in order not to saturate the detector or a concave lens to diffuse the beam. Such an arrangement can be used to decrease the intensity of the beam 1290 and distribute it over a larger area of detection on the detector 1214. For instance, to enable multiple simultaneous measurements from different sensor units that define the detector 1214. In some implementations, the detector (or detectors) 1214 can be a photodiode positioned on the path of the beam when the material is in normal conditions, or it could be a CCD array with different sensitive elements, so that any change in the diffraction angle will result in the beam hitting the detector in different positions. The photodiode or CCD array can be configured to transform the intensity of radiation into intensity of electric current. Moreover, this current can be converted to a voltage, which can then be used as input for the processor. Accordingly the processor can be configured to convert the voltage input into a measure of deformation of the inspected sample.

Figure 13B:
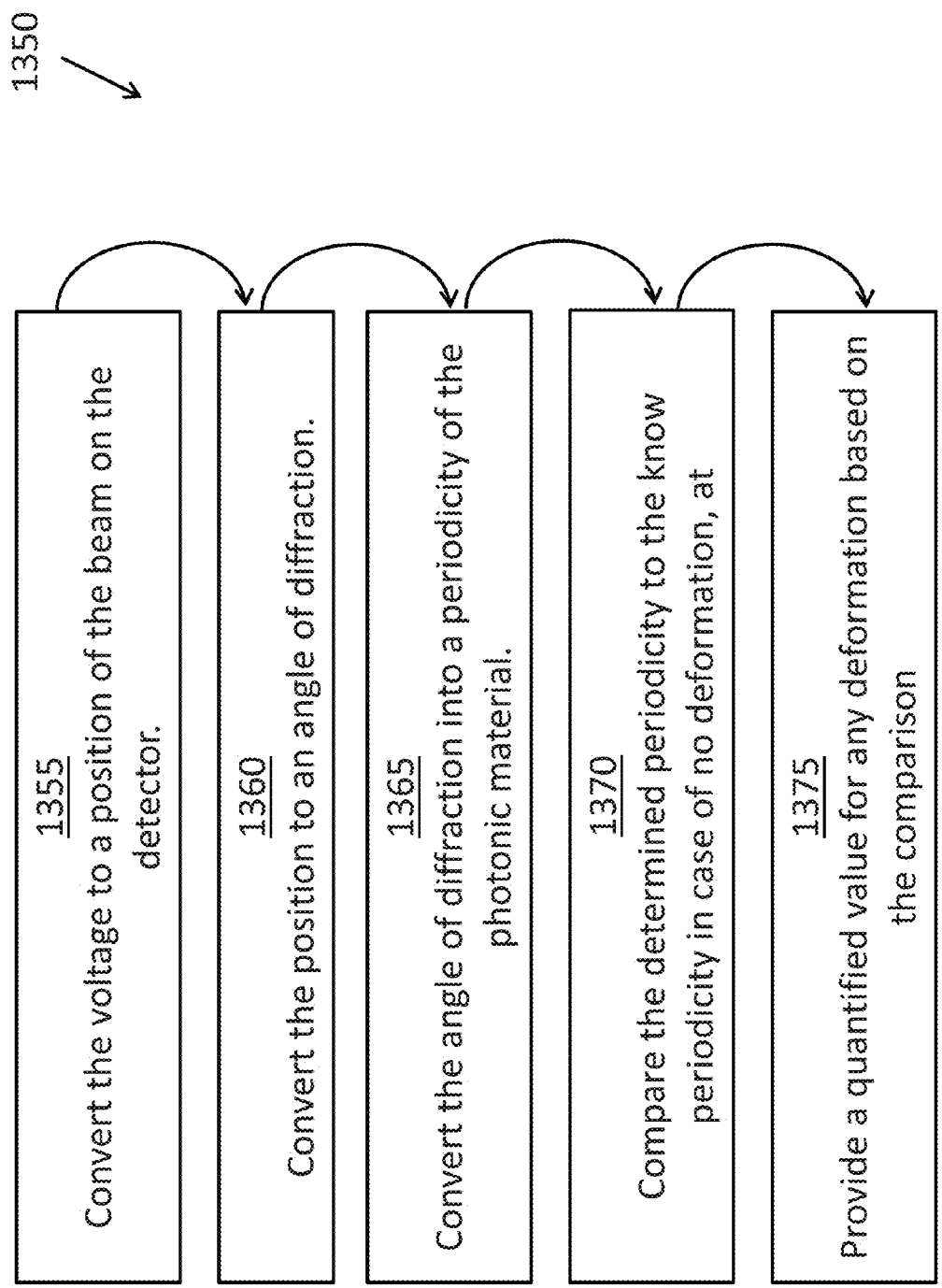
FIG. 13B is a flow diagram illustrating a routine for computing deformation of a photonic structure according to an embodiment of the invention.

More specifically, FIG. 13B illustrates an exemplary routine 1350 performed by the processor for quantifying the deformation of the material. In particular, at step 1355, the processor, which is configured by executing one or more of the software modules 1245, including the analysis software, converts the received voltage into a position of the beam on the detector. For instance, this conversion can be performed as a function of the known location of the sensing elements that comprise the detector 1214. Then, as explained above, at step 1360, the configured processor, based on the geometry of the device, can convert the calculated position to an angle of diffraction. Then at step 1365, the processor converts the angle of diffraction into a periodicity of the photonic material. At step 1370, the processor compares this determined periodicity to the know periodicity in case of no deformation, and, at step 1375, outputs and stores a quantified value for any deformation.

Turning briefly to FIG. 16A-16B, which depict exemplary images (e.g., wavelength maps) of light captured by an exemplary inspection device from inspection of a composite structure constructed in accordance with the disclosed embodiments. FIGS. 16A and 16B are further examples of how an exemplary structural material constructed in accordance with the disclosed embodiments would diffract light, in absence and in presence of a force applied to it. As shown in the FIGS. 16A-16B, the color/shade or diffracted wavelength at each specific point on the material can change depending on the force applied to the material and its deformation. More specifically, FIG. 16A, represents imagery of an inspected material in the situation where the incident white light (or more in general a radiation containing multiple wavelengths) has been reflected and diffracted by the photonic structure described herein as a grating that, in this example, is not under stress. FIG. 16B represents the situation in which the same photonic element or the grating is stretched (e.g., from stress), the spacing is increased and thus the diffraction pattern changes.

The visual map shown in FIG. 16A-16B constitutes an example of the refracted radiation information captured as an input for the inspecting device. After processing and transformation of wavelength to displacement, the output of the inspection device can also be represented as a color map in 2 dimensions if each color is defined to correspond to a certain value of displacement. It has to be noted, however, that the information related to the apparent color or shading of the two exemplary images is provided as an example and can be different. Therefore, input and output could look similar, while containing different information.

In case the analysis is performed with a laser beam, rather than with a diffused radiation, the pattern won't be uniform, but it will consist of regularly distributed spots such as the ones visualized in FIGS. 1 and 4 (e.g., 160A, B, C, D, E, and 465). The 2D image captured as a consequence of diffused irradiation simultaneously provides information on a larger area of sample, as the illuminated area is larger. Conversely, the image of the diffraction pattern generated by the diffraction of the laser beam provides information relative to the area illuminated by the laser. This latter configuration, can be more sensitive and can be advantageous when small displacements are expected to occur uniformly over a larger area of the sample. Alternatively, the diffused irradiation can be used as a preliminary analysis and the laser irradiation as a subsequent more detailed analysis.

FIG. 12B depicts the inspection device 1200 of FIG. 12A from a front perspective view, so that it is possible to visualize the windows 1218 arranged such that the radiation can exit and enter the inspection device 1200. In particular, the window for the collection of the diffracted laser beam is identified as 1218A, the window for the collection of the image as a wavelength map 1218B, the window for the diffused radiation to exit the device is identified as 1218C, and the window for the laser beam to exit the device is identified as 1218D.

Figure 14A:
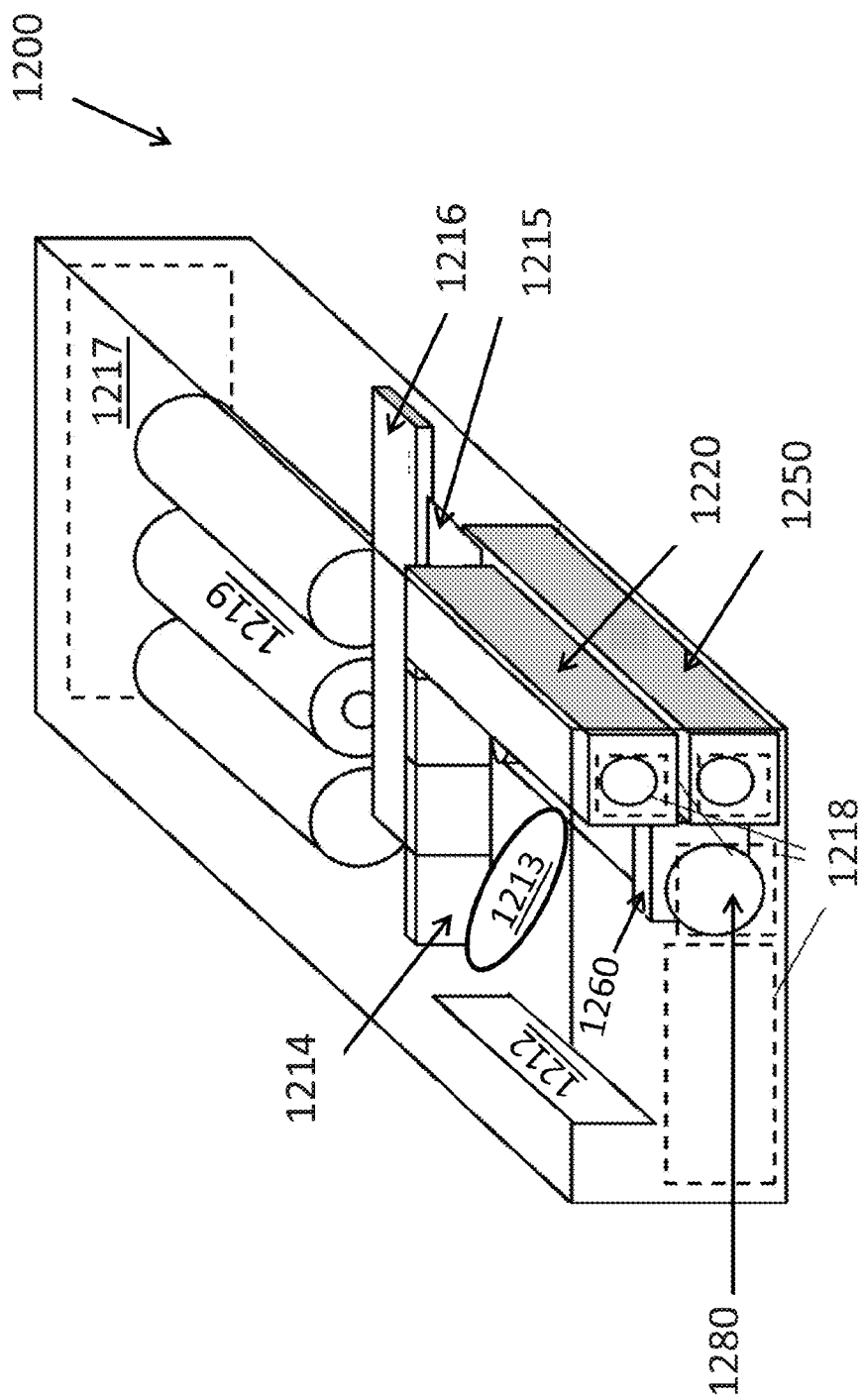
FIG. 14A is a high-level diagram illustrating a front perspective view of an exemplary inspection device according to an embodiment of the invention.
Figure 14B:
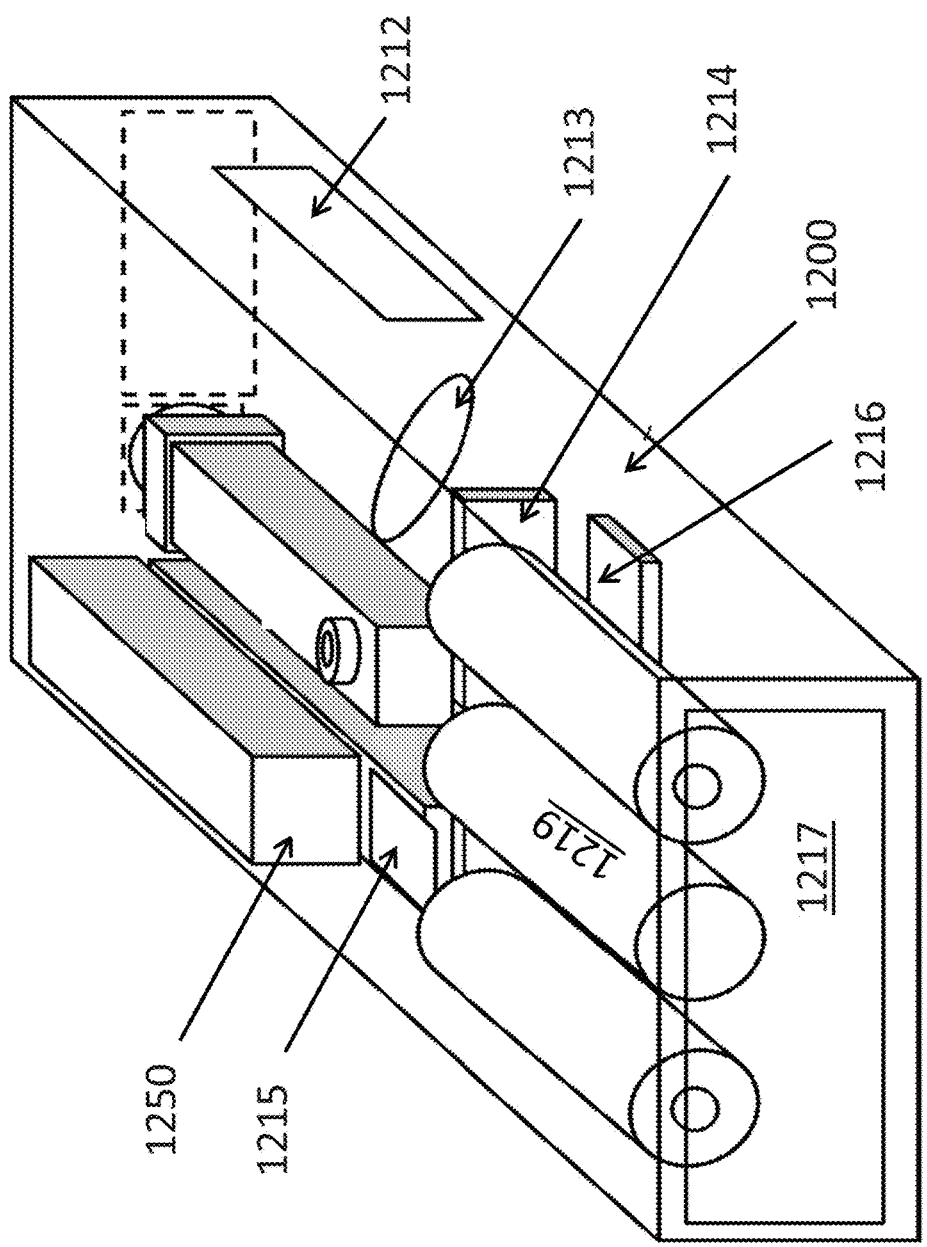
FIG. 14B is a high-level diagram illustrating a rear perspective view of the exemplary inspection device of FIG. 14A according to an embodiment of the invention.

An alternative, more compact arrangement of the components of the inspection device 1200 is depicted in FIGS. 14A and 14B. FIG. 14A is a front perspective view of this variation of the device 1200 in a more compact configuration and FIG. 14B is a rear perspective view. With respect to the particular the elements incorporated into the exemplary compact inspection device configuration and the principles of operation, this exemplary variation is substantially equivalent to the inspection device 1200 depicted in FIGS. 12A and 12B. As such, the respective components are numbered consistently. However, in order to minimize the space utilized, the two light sources are arranged one on top of each other. In particular, the lamp 1250 is represented on top of the laser emitter 1220, however, it can be appreciated that the sources 1250 and 1220 could also have the opposite arrangement. One advantage of having the laser on the bottom is that it is at the same level as the laser detection system, thus it is easier to collect the beam and direct it to the detector if it is on the same plane. Nevertheless, it can be appreciated that additional components for directing the beam to the detection system can be easily incorporated into the inspection device if the light source is not exactly on the same plane as the detector. In addition, the exemplary configuration of the inspection device 1200 shown in FIGS. 14A-14B is also depicted as having batteries 1219 as a power source.

Although the exemplary embodiments are depicted in FIGS. 12A-14B in a high-level (e.g., simplified) form, in accordance with one or more embodiments, the inspection device, can be configured to have a more basic configuration. As noted previously, the inspection device can include only one light source (e.g., 1220 or 1250) and the corresponding detection components and does not necessarily require both types of sources at the same time, as each one of the systems can independently be used to provide quantitative information regarding perturbations. Moreover one or more of the optical elements such as mirrors and lenses can removed without departing from the scope of the disclosed embodiments.

Figure 15A:
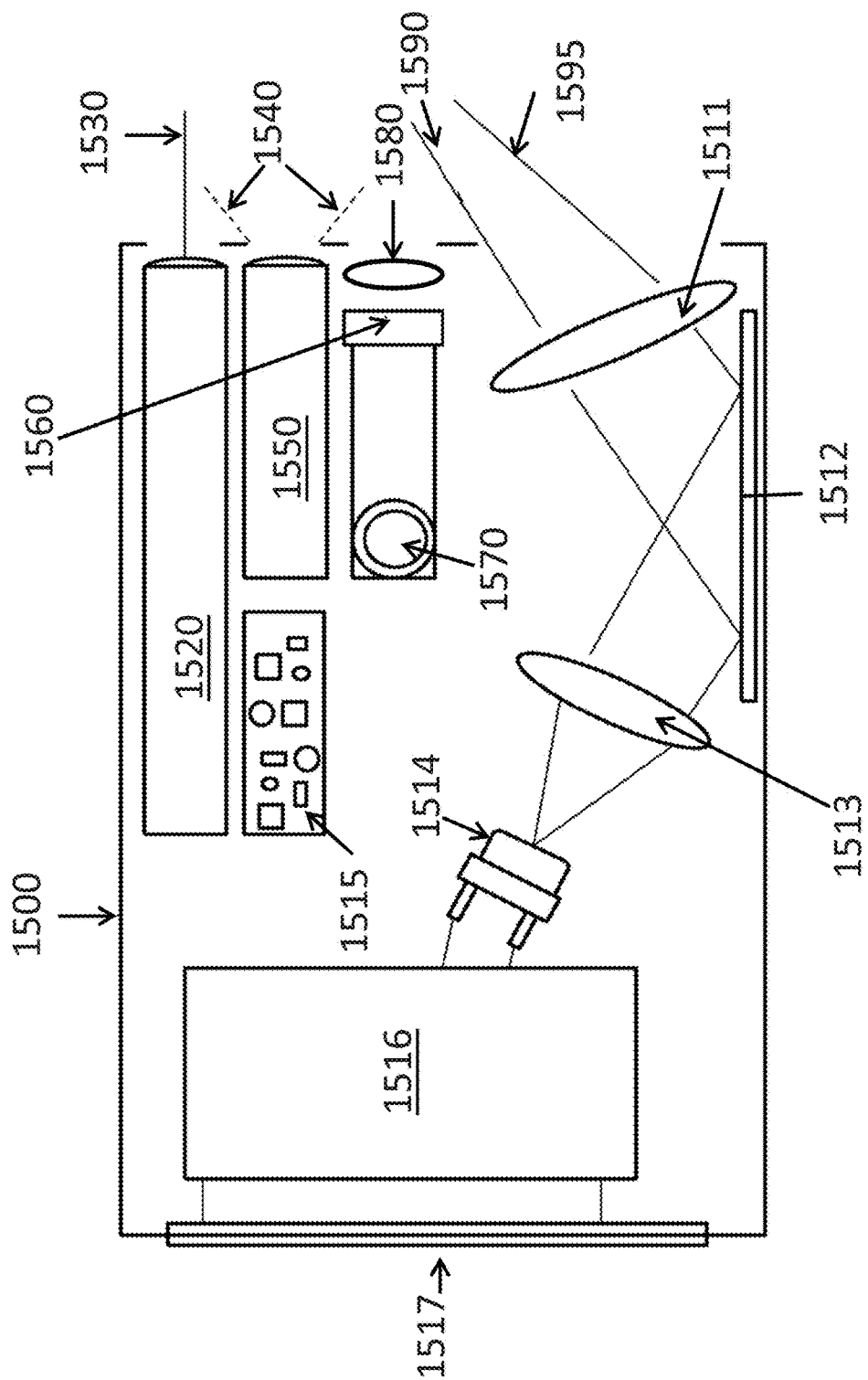
FIG. 15A is a high-level diagram illustrating a top view of an exemplary inspection device according to an embodiment of the invention.
Figure 15B:
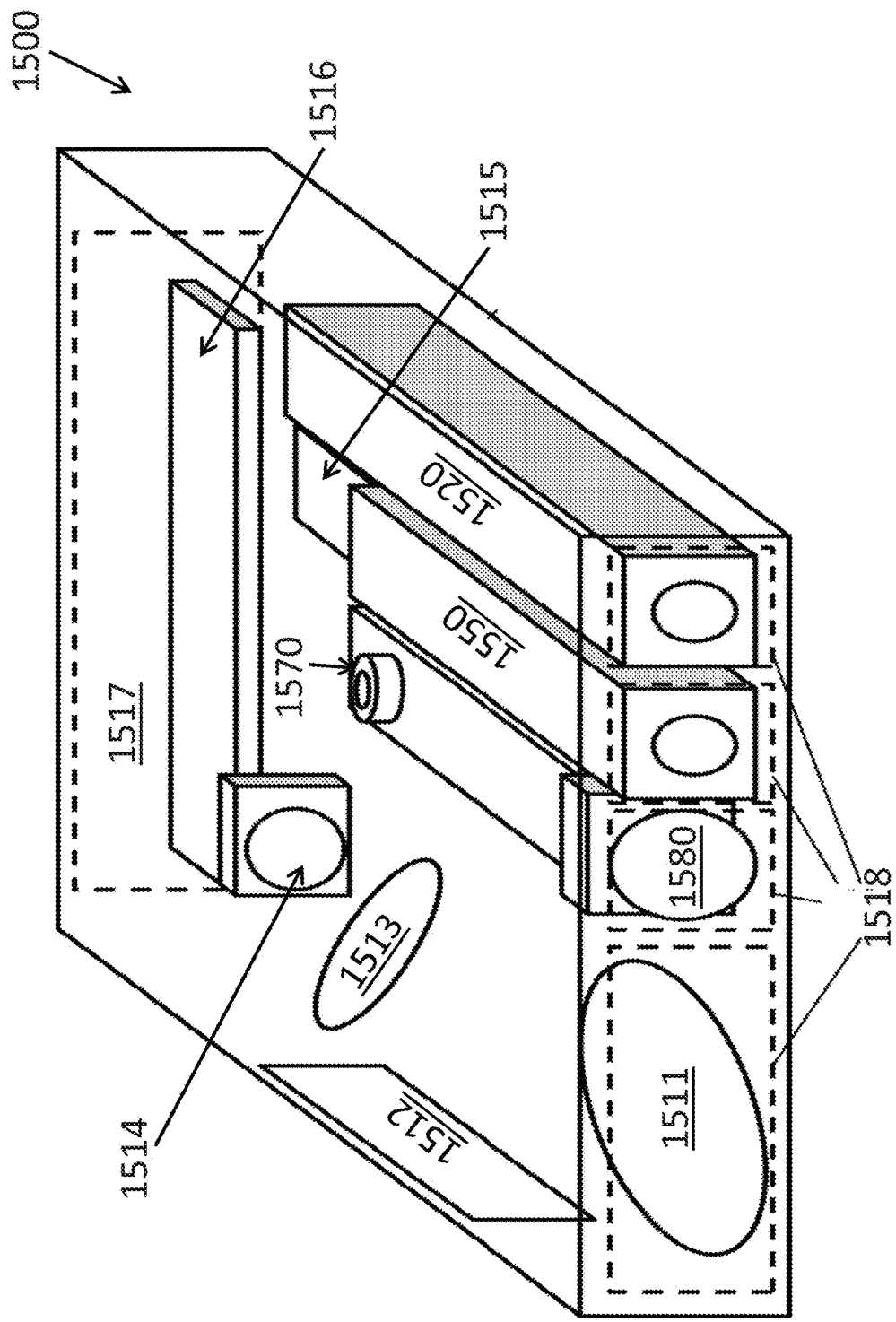
FIG. 15B is a high-level diagram illustrating a front perspective view of the exemplary inspection device of FIG. 15A according to an embodiment of the invention.

Nevertheless, there are other possible embodiments that are configured to implement different systems and methods for detection, which can be advantageous for certain practical applications. In particular, one exemplary alternative option to collect the diffracted laser radiation and direct them to a detector that simply measures the intensity, is to collect more than one diffracted beam and focus them on the detector with a lens, or a system of lenses. A high-level diagram of an exemplary inspection device 1500 having such a configuration is shown in FIGS. 15A and 15B. In particular, FIG. 15A is a top view and FIG. 15B is a front perspective view of the inspection device 1500.

This particular configuration of the inspection device is generally analogous to the configuration described in relation to FIGS. 12A-14B. However, an additional feature is the presence of two lenses 1511 and 1513 disposed on the path of two incoming laser beams 1590 and 1595. In this configuration, both beams are collected by lens 1511, which reduces their divergence or, if possible, can also generate some level of convergence. Both beams are then reflected by the mirror 1512 through another lens 1513. The lens 1513 could be necessary, or not, depending on the initial divergence of the beams and by the power of lens 1511. The purpose of additional lens 1513, if not already achieved through lens 1511, is to focus the two beams on a sensitive part of a photo-diode 1514, which transforms the intensity of the radiation into a current.

In case of deformation of the photonic material, the convergence of the beam onto the photodiode should be compromised. In particular, if the divergence of 1590 and 1595 changes, the focal point or intersection point of the two beams will occur either before or after the photodiode. This will cause an intensity change in the current generated by the photodiode 1514. Accordingly, through calibration, the processor 1516, which is coupled to the photodiode, can be configured to associate a deformation size on the sample material to a given intensity variation measured at the photodiode. A summary of the steps performed by the processor 1516, which is configured by executing an analysis software program, to transform intensity to deformation size can include: calculate the diffraction angle of the beams based on the focus of the two diffracted laser beams on the photodiode and a well-defined divergence angle of the beams at the position of lens 1511. Using equation (1) and the diffraction angle, the configured processor can then calculate the periodicity spacing responsible for such a calculated diffraction angle.

Therefore, a change in the periodicity of the grating caused by a perturbation will result in a change in intensity on the detector. The intensity of electric current generated by the photodiode, which is proportional to the intensity of radiation, can be converted to a voltage and the voltage can be processed by the processor unit 1516 to generate a value of deformation on the material by comparing it to the intensity collected in normal conditions. The calculations performed by the processor are as described in the previous paragraph. This information from the processor can then be sent to a display 1517, which shows the quantitative information relating to the perturbations.

In FIGS. 15A and 15B there are two lenses and one mirror, which, as explained earlier are not always necessary for the operation of the inspection device 1500. Nevertheless, there could be also a higher number of lenses and mirrors to achieve the same function and, in some instances, in a more effective way. For example, if the divergence of the two laser beams is very high, more lenses can be required in order to focus the beam on the detector 1514. For the same reason, more mirrors might be required simply to increase the optical path of the laser beams inside the device in order to achieve the desired convergence. Alternatively, if, for the minimization of space and the optimization of the position of the different elements inside the device, the detector might be in a hard to reach position or hidden behind another element. For this reason more mirrors might be required for the beam or beams to reach the detector or the desired element.

In addition, alternative configurations of the exemplary inspection device can provide more degrees of freedom and a higher level of dimensionality in the measurement of perturbations that are performed. As the photonic materials, for instance the exemplary composite structures previously described, can be configured to have varying dimensionality (e.g., a one, two or three dimensional grating), the inspection device can also be configured to detect and present higher dimensionality. For example, if the photonic material consists of a two dimensional lattice, the inspection device can be configured to detect changes in the angle of diffraction not only on one plane, but on two planes. In such a configuration, the diffracted laser (e.g., beam 1290 of FIG. 12, for example) can move sideways with respect to the detector, and can also move vertically as a function of the perturbation. In this case the angular variations in the diffracted beam won't be only analyzed on the plane of the device, but also in the plane perpendicular to it. Therefore the device will present mirrors, lenses, and detectors setup to receive, work and analyze on beams that are aligned perpendicularly to the plane of FIGS. 13A and 16A. Accordingly, the inspection device can be configured so as to detect this two dimensional movement of the diffracted laser. More specifically, in some implementations, the detector 1214 of the inspection device can be comprised of a planar group of CCD arrays, say, on top of each other, or in any other two dimensional sensing arrangement. The diagram of the system will generally be analogous to the one in FIG. 12 (and also the inspection device of FIG. 14A or 15A, for example), with the only difference that the sensitivity of the device will be enhanced due to the variation in the particular design of the detector. As a result, the inspection device will not only be able to detect the presence of a deformation and quantify it, it will also be able to define the anisotropic shape or directionality of such a deformation, by measuring a displacement along two different directions according to the two dimensional configuration of the device and photonic structure explained above.

Moreover, in order for the inspection device to be used for a three dimensional photonic system such as a photonic crystal described in relation to say, FIGS. 8A-10, the inspection device can be configured to capture and analyze multiple diffraction lines at the same time through different windows and detect the diffraction angle variation. The relative position of the windows with respect to the inspecting beam is defined as a function of the specific structure of the three dimensional lattice or photonic crystal considered. For example, a three dimensional photonic structure with a photonic band gap will generate a diffraction pattern of allowed band and forbidden gaps along different directions determined by the different lattice planes. Therefore, it will be possible to monitor the absence or the decrease of radiation of a certain wavelength along a certain direction. For example, considering a 3D opal with a face-centered cubic (fcc) lattice, this will give rise to a set of photonic stop bands or band gaps, if the quality of the lattice is very high. Few of these stop bands or band gaps are more intense than others and can be collected at angles that are not too different from each other. In particular the stop bands corresponding to the lattice planes having Miller indices of, for instance, 111, 220, and 200, could all be gathered (as explained above) and monitored by the device. Therefore, if there is an increase in intensity corresponding to a specific stop band along a specific direction, this it will indicate that the spacing between the corresponding lattice planes has changed. Furthermore, if the movement of the stop band can be monitored by a 2D detector such as two or more CCD arrays, this will also indicate if the lattice displacement is in compression or extension. According to this possibility to monitor the movement (in angle and intensity) of different stop bands or band gaps independently, this analysis will provide multidimensional information (as many dimensions as the number of stop bands analyzed) about the anisotropy of the deformation occurring inside the lattice along the different directions analyzed.

Although this method would work also without a fluorophore as explained above, the presence of a fluorophore would greatly simplify the measurement. In presence of one or more fluorophores, the incident radiation can target the optical excitation of the fluorophores, so that the analysis can be performed on their emission. In such a scenario, the emission of the fluorophore would be irradiated isotropically in all directions independently on the direction of excitation. However, its intensity would be drastically reduced by the presence of stop bands or band gaps along specific directions determined by the lattice constants or the different planes and wavelength or emission of the one or more fluorophores. Therefore, by conforming the device in such a way that it monitors the absence of intensity along any or all of those directions, it will be possible to determine the presence of displacement by monitoring the intensity change. This would thus provide a multidimensional (as many dimensions as the stop bands analyzed) an anisotropic analysis of the deformation of the material and of any change that determines a variation of the refractive index or emissive properties of one or more or the materials included in the system. These changes could be, for example and without limitation, temperature changes, chemical absorption, functionalization, presence of magnetic fields, exposure to other types of radiations.

Figure 17:
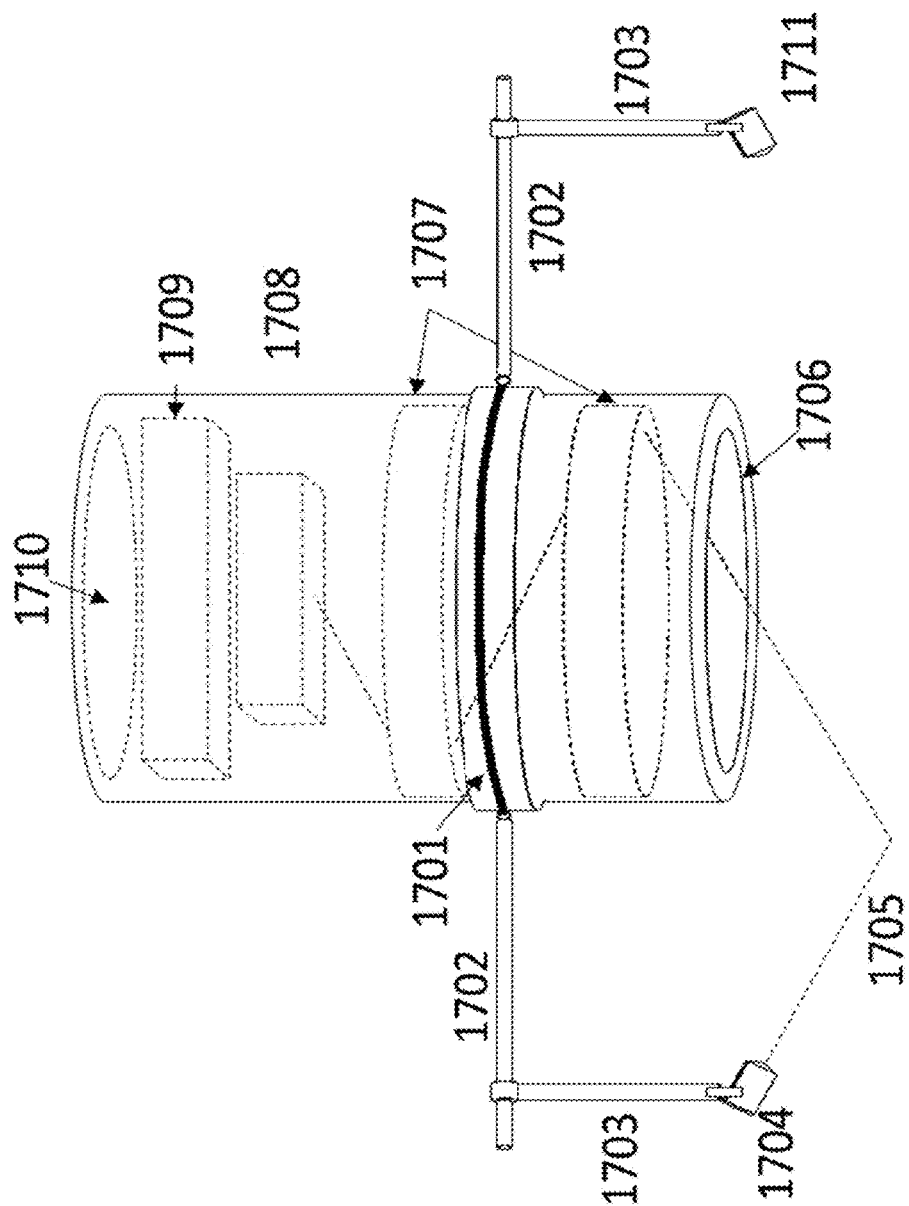
FIG. 17 is a high level diagram illustrating a side perspective view of an exemplary inspection device comprising radiation sources with adjustable positions over at least 2 degrees of motion according to an embodiment of the invention.
Figure 18:
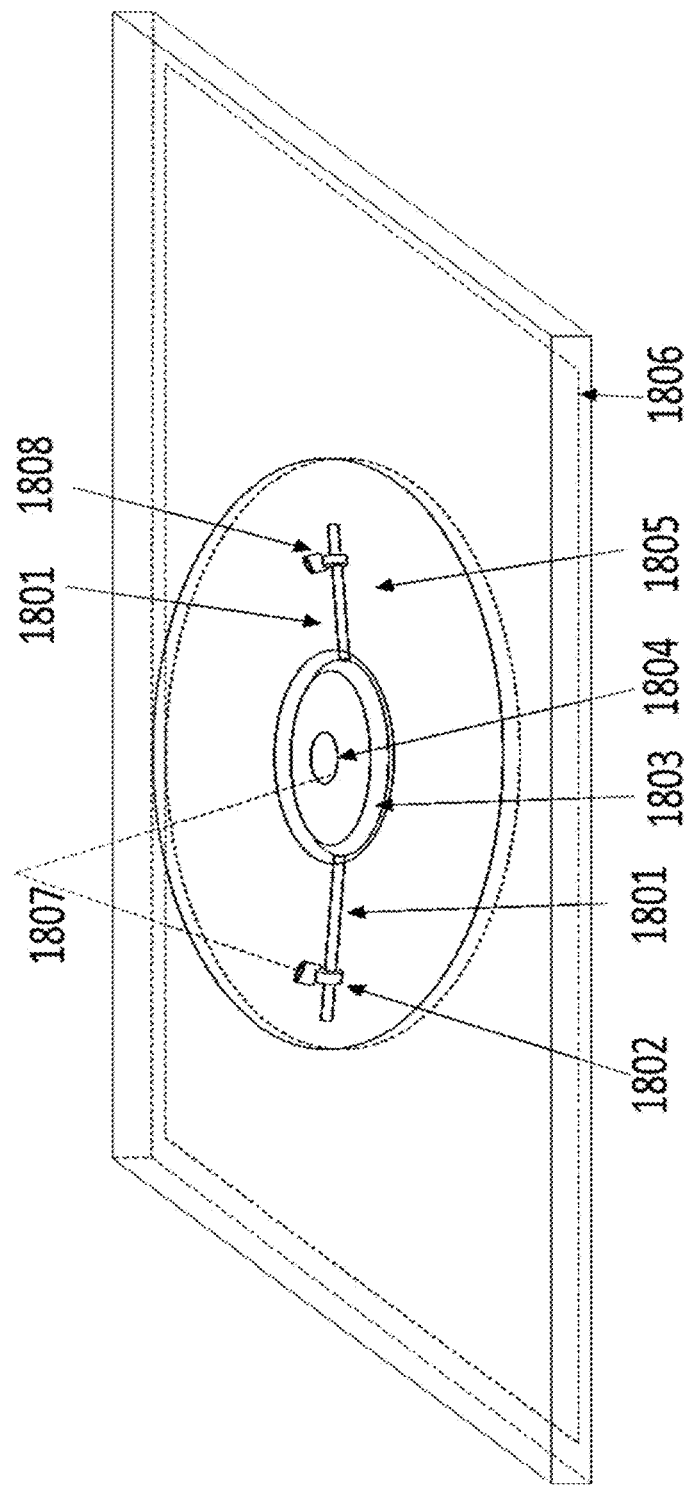
FIG. 18 is a high level diagram illustrating a bottom-side view of an exemplary inspection device with positionable radiation sources according to an embodiment of the invention.

Two other practical implementations of the disclosed embodiments of the invention are represented in FIGS. 16 and 17. The main difference between these exemplary inspection devices and the previously described inspection devices is the capability to move the light source. In FIG. 16 the light source can be a diffuse radiation source 1701 or a laser 1704, or both at the same time. Such source is attached to a movable arm 1703 which can slide over another arm 1702, in order to adjust its distance from the body of the device, which in this figure is represented as cylindrical. Arm 1702 can rotate around the device and is held in place by a railing system 1601 placed around the device. The radiation emitted by the source 1704 is indicated as 1705, this is diffracted from the material and sent into the device following a possible path traced by the dotted line 1705. Such a radiation will enter the device from a window 1706 and potentially be reflected by one or more mirrors 1707 to reach the detector 1708. Even in this case the presence of the mirrors is not required, but it could facilitate the optimization of the architecture of the device. 1709 is the processor and 1710 a touch screen or a simple screen for the visualization of the data and results. The advantage of having a camera moving with respect to the sensor is that it makes it easy to collect radiation from different directions and thus monitor different diffraction conditions (for 2 dimensional photonic materials) or different stop bands/band gaps (for 3 dimensional photonic materials). Even in this case, if the light source is diffused, the camera sensor that can be placed in proximity of the window 1706 will monitor changes in the wavelength diffracted at each point, while if the source is a laser, the absence and presence of radiation, or the intensity of radiation will provide information regarding the displacement of the material.

In FIG. 17 the principle utilized is the same, the main difference is that this embodiment focuses on the user interface. The entire system can be adapted and miniaturized on a device similar to a tablet here represented. The dashed line 1806 represents a touch screen on the device on the opposite side with respect to the current view. The back side of the device here appearing on the top of the figure includes the light sources 1802 and 1808 on movable arms that can rotate in circle around a certain spot. This spot doesn't necessarily have to be in the center of the device, but it can be located as it is more convenient. The light sources can also slide along the movable arms 1801 so that they can be placed anywhere on a circular area 1805 and thus cover several diffraction angles. The rotating arm can move around a circular support 1803. In case the radiation source is a laser 1802, one of the possible paths of the beam is traced by a dashed line: it is reflected and diffracted by the photonic material and redirected toward window 1804 of the device which can be the sensitive element of the detector itself, or a window that lets the beam through to the detector or to one or more mirrors as shown in the previous embodiments. If the diffused light source is utilized, the image of the diffraction pattern will be analyzed by a camera sensor 1804. It is to be noted that element 1804 can be either the camera sensor, or photodetector, or both, or a window that lets the radiation through, so that it can reach the opportune sensitive element either directly or with a set of mirrors, or other optical elements.

At this juncture, it should be noted that although much of the foregoing description has been directed to systems and methods for providing composite structures, the systems and methods disclosed herein can be similarly deployed and/or implemented in scenarios, situations, and settings far beyond the referenced scenarios.

It should be appreciated that more or fewer operations can be performed than shown in the figures and described. These operations can also be performed in a different order than those described. It is to be understood that like numerals in the drawings represent like elements through the several figures, and that not all components and/or steps described and illustrated with reference to the figures are required for all embodiments or arrangements.

Thus, illustrative embodiments and arrangements of the present systems and methods provide a system and a computer implemented method, computer system, and computer program product for wirelessly configuring field devices. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A composite photonic structure, comprising:
   one or more layers of a structural material;
   a diffractive grating in registry with the one or more layers of structural material, the grating including a plurality of features that are arranged to have periodicity in at least one dimension; and
   a fluorophore material disposed within the composite structure.

2. The structure of claim 1, wherein the grating is one or more of:
   a discrete layer of one or more grating materials disposed over an entire surface of the one or more layers of structural material, and
   defined by a surface of the one or more layers of structural material, and wherein the structural material is a non-metallic material.

3. The structure of claim 2, wherein the grating extends over one or more of a top surface and a bottom surface of at least one of the one or more layers of structural material.

4. The structure of claim 2, wherein the grating layer separates two layers of structural material.

5. The structure of claim 1, wherein the plurality of features of the grating are arranged to have periodicity in at least two dimensions.

6. The structure of claim 1, wherein the fluorophore is of the type that is excited by radiation having a first wavelength and emits radiation having a second wavelength upon excitation, and wherein the one or more layers of structural material and the grating are at least partially transparent to radiation having the first and second wavelengths.

7. The structure of claim 6, wherein the fluorophore is incorporated into the structure as one of: a separate layer of material that includes at least the fluorophore material, and a dopant or nano-material that is embedded in a region within at least one of the one or more layers of structural material.

8. The structure of claim 7, wherein the fluorophore material is arranged within the composite structure to have consistent periodicity in at least one dimension.

9. The structure of claim 7, wherein the fluorophore material extends throughout a cross-sectional area of the composite structure.

10. The structure of claim 6, further comprising;
a first set of elongate rods including the fluorophore material embedded within the one or more structural material layers, wherein the rods in the first set are oriented parallel to one another and are spaced apart to have consistent periodicity in at least one dimension.

11. The structure of claim 10, further comprising;
a second set of elongate rods including the fluorophore material embedded within the one or more structural material layers, wherein the rods in the second set are oriented parallel to one another and are spaced apart to have consistent periodicity in at least one dimension, and wherein the second set of rods are oriented perpendicular to the first set of rods.

12. The structure of claim 6, wherein the grating is a layer of one or more grating materials and wherein the fluorophore material is provided within the grating layer.

13. The structure of claim 6, wherein the fluorophore layer is arranged between the one or more layers of structural material thereby separating two layers of structural material.

14. The structure of claim 6, wherein the fluorophore material is fluorophore is embedded within the structural material as one or more of: a dopant and a nano-material.

15. The structure of claim 1, wherein the grating features have periodicity as defined by a first value, and wherein the first value is defined as function of a size of perturbations to be detected during use of the composite structure.

* * * * *